United States Patent [19]

Harms et al.

[11] Patent Number: 4,874,915

[45] Date of Patent: Oct. 17, 1989

[54] APPARATUS FOR THE RAPID MICROWAVE THAWING OF CRYOPRESERVED BLOOD, BLOOD COMPONENTS, AND TISSUE

[75] Inventors: Frank M. Harms, Marietta; Victor Tripp, Tucker; Thomas B. Wells, Smyrna, all of Ga.

[73] Assignee: Lifeblood Advanced Blood Bank Systems, Inc., Atlanta, Ga.

[21] Appl. No.: 292,574

[22] Filed: Dec. 30, 1988

[51] Int. Cl.$^4$ ............................................. H05B 6/80
[52] U.S. Cl. ..................... 219/10.55 F; 219/10.55 A; 604/114; 604/409
[58] Field of Search ................. 219/10.55 F, 10.55 A, 219/10.55 R, 10.55 M, 10.55 E, 10.55 D; 604/113, 114, 403, 408, 409; 128/399, 804

[56] References Cited

U.S. PATENT DOCUMENTS

| | | | |
|---|---|---|---|
| Re. 31,241 | 5/1983 | Klaila | 219/10.55 R |
| 3,288,894 | 11/1966 | Deaton | 219/10.55 F |
| 3,474,209 | 10/1969 | Parker | 219/10.55 A |
| 3,809,845 | 5/1974 | Stenstrom | 219/10.55 M |
| 3,889,009 | 6/1975 | Lipoma | 219/10.55 AX |
| 3,920,945 | 11/1975 | Smith et al. | 219/10.55 R |
| 3,963,892 | 6/1976 | Camph et al. | 219/10.55 A |
| 4,037,071 | 7/1977 | Kaufman, Jr. et al. | 219/10.55 F |
| 4,128,751 | 12/1978 | Sale | 219/10.55 A |
| 4,165,455 | 8/1979 | Mayfield | 219/10.55 A |
| 4,272,663 | 6/1981 | Green | 219/10.55 E |
| 4,303,820 | 12/1981 | Stottmann et al. | 219/10.55 F |
| 4,310,738 | 1/1982 | Moretti et al. | 219/10.55 A |
| 4,310,739 | 1/1982 | Hatem | 219/10.55 A |
| 4,316,070 | 2/1982 | Prosise et al. | 219/10.55 E |
| 4,323,745 | 4/1982 | Berggren | 219/10.55 A |
| 4,336,435 | 6/1982 | Kashyap et al. | 219/10.55 F |
| 4,401,873 | 8/1983 | Berggren et al. | 219/10.55 A |
| 4,492,839 | 1/1985 | Smith | 219/10.55 R |
| 4,503,307 | 3/1985 | Campbell et al. | 219/10.55 E |
| 4,629,847 | 12/1986 | Gics | 219/10.55 A |
| 4,640,280 | 2/1987 | Sterzer | 128/804 |
| 4,652,712 | 3/1987 | Zeipel | 219/10.55 F |
| 4,742,202 | 5/1988 | Campbell et al. | 219/10.55 F |
| 4,752,663 | 6/1988 | Meisel | 219/10.55 F |
| 4,801,777 | 1/1989 | Auerbach | 219/10.55 M |

OTHER PUBLICATIONS

Burdette, E. C. & Jones, J. R., *Design of Microwave Illuminators for Thawing of Frozen Erythrocytes*. Project A-2210, Biomedical Research Group, Georgia Inst. of Technology (Jun. 1979).
Burdette, E. C. & Gonzales, A., *Design of Microwave Illuminator for Thawing of Frozen Plasma*. Project A-2210, Phase II, Biomedical Research Branch, Georgia Inst. of Technology (Apr. 1980).
Rock, G., Thackaberry, E. S., Dunn, J. G., and Kashyap, S., *Rapid controlled thawing of fresh-frozen plasma in a modified microwave oven*. Transfusion vol. 24, No. 1 (Jan.-Feb. 1984) J. B. Lippincott Company.
Leaman, P. L. and Martyak, G. G., *Microwave Warming of Resuscitation Fluids*. Annals of Emergency Medicine (Sep. 1985) pp. 876-879.

Primary Examiner—Philip H. Leung
Attorney, Agent, or Firm—Jones, Askew & Lunsford

[57] ABSTRACT

An electromagnetic illuminator for the rapid thawing of cryopreserved plasma comprises a source for electromagnetic energy and a hollow waveguide having an aperture at one end for propagating and dispersing the electromagnetic waves over a predetermined area. The hollow waveguide is loaded with a liquid dielectric material having dielectric properties substantially the same as frozen plasma. A focusing medium refracts the electromagnetic waves propagating within the waveguide to provide a substantially uniform electromagnetic field across the waveguide aperture. A flexible membrane covers the aperture of the waveguide to contain the liquid dielectric material. The container of plasma to be thawed is placed against the membrane covering the aperture, and a hollow cap assembly filled with the liquid dielectric material is translated against the side of the plasma container distal to the microwave source. The container of plasma is thawed by the uniform electromagnetic field at the aperture of the waveguide. The liquid dielectric material loading the horn and cap eliminates dielectric discontinuities and serves as a thermal damper to dissipate localized heat buildup in the plasma being thawed.

64 Claims, 7 Drawing Sheets

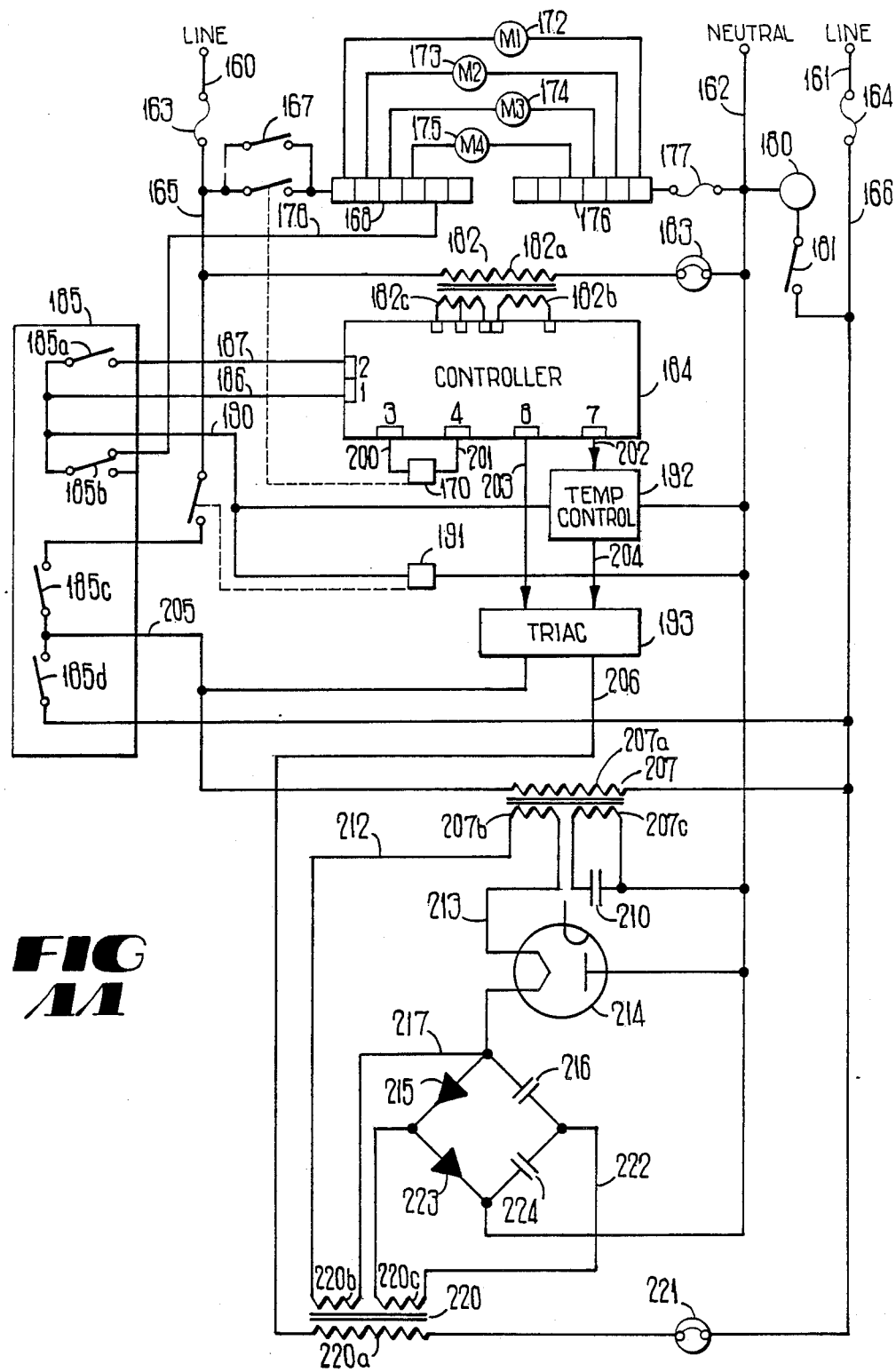
FIG. AA

APPARATUS FOR THE RAPID MICROWAVE THAWING OF CRYOPRESERVED BLOOD, BLOOD COMPONENTS, AND TISSUE

TECHNICAL FIELD

The present application relates generally to a method and apparatus for thawing a frozen substance, and relates more specifically to a method and apparatus for the rapid and hygienic thawing of fresh-frozen blood, blood components, and tissue by electromagnetic illumination.

BACKGROUND OF THE INVENTION

A readily available supply of plasma is an essential requirement of any medical trauma treatment facility. Since plasma can be stored at room temperature for only a matter of a few hours before spoilage occurs, it is conventional practice to freeze plasma. Typically, plasma is frozen within six hours after collection, in polyvinyl chloride bags holding about 250 milliliters. The fresh-frozen plasma is subsequently stored at temperatures of around −30° C. When properly frozen, plasma may be stored for up to five years.

While the procedure of fresh-freezing plasma has essentially solved the problems of storing plasma, the process of thawing the frozen plasma for use presents certain difficulties. When other components of blood, such as whole blood or platelets, are being thawed, possible damage to cells during thawing is a major concern. For plasma, however, post-thaw viability of cellular structures is not of concern, but the viability of coagulation proteins is of primary importance. The most widely accepted method of thawing fresh-frozen plasma comprises immersing the bag of frozen plasma in a warm-water bath. By completely surrounding the bag of froze plasma in a 30° C.-37° C. water bath and agitating it periodically, a single bag or "unit" of frozen plasma may be thawed usually in thirty to forty-five minutes.

This procedure presents a number of problems. First, immersing the bag in a non-sterile water bath may contaminate the bag ports, such that the thawed plasma is tainted as it is withdrawn from the bag. Additionally, any interruption in the integrity of the bag can permit water to enter the bag, thereby contaminating the plasma. Further, the water bath process cannot be accelerated, such as by exposing the plasma to a higher temperature bath, since subjecting the frozen plasma to any larger thermal gradient in an effort to speed up the procedure can result in physical stress and possible damage to the normal protein configuration of the plasma. The requirement of a thawing period of from thirty to forty-five minutes renders the use of frozen plasma impractical for emergency trauma cases, where the patient may have an immediate need for plasma and cannot afford the luxury of waiting for frozen plasma to be thawed. As a result, it is a frequent practice for medical facilities to anticipate possible plasma needs by thawing a number of units of plasma in advance. However, since plasma cannot be safely refrozen once thawed, units which are thawed in anticipation of possible use must be discarded if the anticipated use does not arise.

Accordingly, there is a need to provide a hygienic method and apparatus for the thawing of fresh-frozen plasma which does not expose the ports or the contents of the bag to the possibility of contamination.

There is a further need to provide a method and apparatus for the thawing of fresh-frozen plasma which is sufficiently rapid that plasma can be kept frozen until only moments before it is actually needed.

A number of efforts have been made to adapt microwave ovens for thawing frozen blood components which are contained in a bag. Some of these efforts have involved attempts to adapt a conventional cavity-type microwave oven, of the type widely used for cooking foods, for use in thawing such blood components. However, it is well known that cavity-type microwave ovens suffer a number of disadvantages which, while merely an inconvenience in thawing frozen food, become of critical importance when thawing frozen components of blood for medical purposes. In a cavity resonator, microwaves bounce off the walls of the cavity. Superimposed incident and reflected waves can produce standing waves. At some locations within the cavity the incident and reflected electromagnetic waves reinforce one another, and at other locations the incident and reflected waves cancel. Thus, a typical resonant cavity may contain a number of electromagnetic "hot" spots where the incident and reflected waves reinforce one another, as well as a number of electromagnetic "cold" spots where the incident and reflected waves cancel one another. This uneven electromagnetic field pattern across the oven cavity will tend to heat some portions of a substance placed in its interior more rapidly than others, resulting in nonuniform thawing of the substance.

As if this were not problem enough, many substances, including plasma, exhibit widely varying absorption and dielectric characteristics as they change state from a solid to a liquid. Liquid plasma will absorb electromagnetic energy nearly seventeen times faster than frozen plasma. Thus, in an unevenly heated quantity of frozen plasma, as one particular portion of the material begins to thaw and changes to a liquid, it will begin absorbing electromagnetic energy considerably faster than its still-frozen surroundings. Further, as the amount of energy absorbed by the liquid plasma increases, the amount of remaining energy available to heat the adjacent frozen areas decreases. Thus, not only is the liquid plasma heated faster, but the adjacent areas of frozen plasma are heated even slower. This variation in absorption characteristics exacerbates the problem of uneven heating and results in a phenomenon known as "thermal runaway".

In addition, reflections of electromagnetic waves also occur at the interface between two insulating materials having differing dielectric or magnetic properties. Liquid plasma has a dielectric constant approximately ten times that of frozen plasma. Thus, as a quantity of frozen plasma is heated with microwaves, a dielectric discontinuity is created at the interface between liquid and solid plasma. An electromagnetic wave incident on such a boundary surface is partly transmitted into the second material and partly reflected back into the first. This reflection disrupts the electromagnetic field and can cause further uneven heating of the fresh-frozen plasma.

A number of efforts have been made to overcome these problems of nonuniform heating in a cavity-type resonator. In one method, a bag of plasma was exposed in a microwave oven for a number of thirty second periods. Between exposure periods, the bag was removed from the oven and manually manipulated for ten seconds to attempt to intermix any unevenly heated portions of the bag's contents. However, this method did not eliminate the problem of thermal runaway during the period of exposure to the microwave energy, and manual manipulation of the bags tended to produce inconsistent results.

In an effort to overcome these problems, an apparatus disclosed in U.S. Pat. No. 4,336,435 provides four rotary shafts in the oven cavity. A bag of plasma is clamped into a special bag holder, which in turn is snapped onto one of the rotary shafts. Each of the four rotary shafts is capable of accommodating a bag holder, permitting up to four bags to be thawed simultaneously. During thawing, the rotating shafts subject each bag to a rotary oscillating motion. While the plasma is solid, the agitation moves the plasma to avoid continuous exposure of any portion of the plasma to microwave "hot" or "cold" spots. As the plasma begins to thaw, the agitation purports to intermix the frozen and thawed portions of the plasma in an effort to attain temperature uniformity. A temperature probe associated with each rotary shaft monitors the temperature of each bag to avoid overheating. However, the apparatus imparts little motion to the bag adjacent to the axis of rotation of the rotary shift. Agitation of the plasma near the axis of rotation and movement of such plasma through microwave "hot" and "cold" spots is therefore not afforded. The apparatus is thus not completely effective in preventing overheating of localized portion of the plasma. Further, so that the bag of plasma will fit within the bag holder, the plasma must be frozen in a special clamping device to ensure an acceptable bag configuration, and bags frozen in an irregular shape cannot be accommodated by this apparatus.

In yet another attempt to adapt a cavity-type microwave oven for thawing plasma, U.S. Pat. No. 4,742,202 discloses a device mounted within the cavity of the oven which includes a tray for holding a bag of plasma. The tray travels around a three-dimensional circuitous track having peaks and valleys with respect to the oven floor. Simultaneously with travelling around this track, the tray may be rocked back and forth across a horizontal plane. Transporting the container of plasma around the track on the rocking ray avoids continuous exposure of the plasma to microwave "hot" and "cold" spots within the oven cavity. In addition, the transporting purports to agitate the plasma container sufficiently to cause a mixing between the warm and cold portions of the liquid. However, this apparatus has also not been completely effective in avoiding overheating of localized portions of the plasma. Further, this apparatus employs a bag holder similar to that disclosed in the aforementioned U.S. Pat. No. 4,336,435 and thus requires the plasma bags to be frozen in a configuration acceptable for accomodation by the bag holder.

A further complication inherent in using a cavity-type microwave oven concerns variations in the exposure time of a frozen substance depending upon the quantity of the substance involved. In a cavity-type resonator, electromagnetic waves will tend to continue bouncing around the interior of the cavity until they are absorbed by the material being thawed. If two bags of plasma are exposed within the oven at the same time, some of the microwave energy which would have otherwise reflected around inside the cavity until being absorbed by the first bag will instead be absorbed by the second bag and never reach the first bag. Thus, it takes longer for each bag to thaw, and exposure times for units of fresh-frozen plasma within a cavity-type microwave oven must therefore be controlled to take into account the total quantity of material being thawed. Given the urgency which often attends trauma care, the possibility of error in miscalculating the exposure time of a given quantity of frozen material is introduced. For example, if only a single bag of plasma is introduced into an oven set to operate for the time required to thaw two bags, overheating and damage to the material being thawed would result.

In the aforementioned U.S. Pat. No. 4,336,435, temperature probes associated with each rotary shaft are intended to take into account variations in the quantity of plasma being thawed by monitoring the temperature of each bag and controlling exposure time to prevent the plasma from being overheated. However, as previously suggested, this apparatus is not completely effective in preventing damage to the plasma during thawing, since the probe can measure the temperature at only a single point on the bag and cannot sense localized overheating in remote locations within the bag.

Thus, there is a need to provide a microwave apparatus for the rapid thawing of frozen plasma which avoids uneven heating of the material being thawed and which eliminates the possibility of error arising from variations in exposure time according to the volume of material being thawed.

Efforts have been made to devise an apparatus which overcomes the problems associated with cavity-type microwave ovens. In one such apparatus, a microwave illuminator comprising an upwardly-facing horn antenna has a microwave source disposed in its base. The horn disperses the microwaves across its cross-sectional area, thereby providing a electromagnetic field of approximately uniform intensity across the horn aperture. Additionally, the horn guides the microwaves in a substantially linear path, minimizing reflection of the microwaves and thereby eliminating the standing wave caused by superposition of incident and reflected waves. Thus, microwave "hot" and "cold" spots are minimized. The horn is filled with granular silica, or sand, a semi-solid material having a dielectric constant substantially equal to the dielectric constant of frozen plasma. The bag of frozen plasma is set in the mouth of the horn directly on top of the sand loading the horn. The granular silica permits an efficient coupling of the microwave energy into the bag of frozen plasma, since it minimizes dielectric discontinuities between the microwave source and the contents of the bag. Additional sand is then poured over the top of the bag of plasma to minimize the dielectric discontinuity along the surface of the bag distal to the microwave source. The sand loading the horn and surrounding the bag of plasma serves to couple the microwave energy to the frozen plasma efficiently.

This illuminator design suffers a number of disadvantages, however, First, to minimize the dielectric discontinuities between the bag of frozen plasma and the sand upon which it rests, special care must be taken when freezing the plasma to ensure that the bag is perfectly flat. Any container of plasma frozen in an irregularly shaped configuration will cause air spaces between the bag and the sand, creating a dielectric discontinuity which will reflect a portion of the incident wave and thereby contribute to nonuniform heating. Additionally, after continued use, the sand in the horn becomes packed down, changing the dielectric characteristics of the horn load and disrupting the power distribution. Further problems arise from the direct contact between the bag and the sand. The requirement of pouring sand over the bag is messy and can lead to irregular results. And, any condensation on the exterior of the cold bag could cause sand to stick to the bag ports so as to contaminate the plasma when it is later withdrawn. Finally, the sand surrounding the bag serves as a thermal insulator, preventing any localized heat build-up from dissipating.

Thus, there is a need to provide an electromagnetic illuminator which quickly, safely, and hygienically thaws frozen plasma.

There is also a need to provide an electromagnetic illuminator for thawing frozen plasma which accommodates irregularly-shaped bags.

There is yet another need to provide an electromagnetic illuminator which eliminates dielectric discontinuities but which does not thermally insulate the product being thawed so as to aggravate thermal runaway.

SUMMARY OF THE INVENTION

As will be seen, the present invention overcomes these and other problems associated with prior art methods and apparatus for the thawing of fresh-frozen plasma. Stated generally, the present invention provides a hygienic method and apparatus for the rapid thawing of frozen blood components which will not contaminate the bag or its ports. The method and apparatus permit rapid thawing, thereby permitting the plasma to remain frozen until it is actually needed and to be thawed within two minutes after being taken out of the freezer. The method and apparatus provides for a uniform heating of the material being thawed, and thawing time is independent of the quantity of material begin thawed.

Stated somewhat more definitely, the present invention comprises a method and apparatus for the rapid and hygienic thawing of fresh-frozen plasma by electromagnetic illumination. The apparatus of the invention comprises an electromagnetic illuminator which provides a uniform electromagnetic field surrounding the material to be thawed. The media through which the electromagnetic waves propagate are dielectrically homogeneous and have dielectric characteristics substantially identical to the frozen plasma. Thus, the frozen plasma is effectively coupled to the electromagnetic field. The combination of the uniform magnetic field and the efficient coupling of the energy into the frozen plasma provides a uniform thawing of the plasma. The apparatus prevents any microwave energy not absorbed by the frozen plasma on the first pass from reflecting back into the plasma and disrupting the energy field. Finally, the apparatus provides a thermal damping effect which absorbs and dissipates any localized overheating so that the plasma will thaw uniformly.

Stated more specifically, the apparatus of the present invention comprises a hollow wave guide having an electromagnetic energy source selectively operable to emit electromagnetic waves disposed in one end thereof. The wave guide projects and conveys the electromagnetic waves and disperses the waves across an aperture at the opposite end of the wave guide. The waveguide accomplishes a substantially uniform power distribution across the aperture by any one or a combination of several approaches. First, the mode of electromagnetic wave propagation provided by conventional RF horns provides a power distribution at the aperture which is distinctly "center heavy," that is, the power distribution is highest in the center of the aperture and tapers off toward the edges in the direction of electromagnetic intensity of the waves, i.e. in the H-field direction. To overcome this uneven power distribution, the waveguide of the preferred embodiment of the present invention confines and guides the microwaves to propagate in a plurality of odd-numbered modes of propagation, e.g. in the first, third, and fifth modes. The waveguide is configured such that the comulative effect of this plurality of odd-numbered modes of propagation creates an approximately uniform electromagnetic field across the waveguide aperture. Alternatively, the present invention contemplates using a power redistribution device, either with a conventional horn or with the multiple odd-numbered mode waveguide of the preferred embodiment, to modify the electromagnetic field at the waveguide aperture to provide a more uniform power distribution. This power redistribution can be accomplished either reflectively or refractively. For example, a grid of metal wires can be placed across the waveguide in the direction of the E-field, with the spacing between adjacent wires controlled to reflect energy at high energy locations and to pass energy at lower energy locations. Alternatively, a differential dielectric lens comprising optical elements of varying dielectric characteristics can be disposed across the aperture to refract the waves, or the sides of the horn adjacent the aperture can be loaded with a material having a different dielectric constant to accomlish similar refraction.

To eliminate dielectric discontinuities at the surface of the plasma bag which can cause reflections and disrupt the energy field, the plasma bag is encapsulated between membranes comprised of a material having similar dielectric properties as the frozen plasma. Further, the wave guide is loaded with a liquid dielectric material having dielectric properties substantially equal to the dielectric properties of the material encapsulating the frozen plasma. Thus, all dielectric discontinuities are eliminated between the electromagnetic energy source and the container of frozen plasma placed at the aperture of the wave guide. A cap assembly filled with the same liquid dielectric material is positioned over the aperture of the wave guide to eliminate dielectric discontinuities along the surface of the plasma container distal to the electromagnetic energy source. The container of plasma is thus exposed to an electromagnetic field of substantially uniform intensity, avoiding the problems of electromagnetic "hot" and "cold" spots. In the event of any localized overheating, the liquid dielectric material serves as a thermal damper, absorbing and dissipating any uneven heating within the frozen plasma so that the plasma will heat uniformly.

Thus, it is an object of the present invention to provide an improved method and apparatus for thawing fresh-frozen plasma.

It is a further object of the present invention to provide a method and apparatus for the thawing of fresh-frozen plasma which is sufficiently rapid that plasma can be kept frozen until only moments before it is actually needed.

It is another obejct of the present invention to provide a hygienic method and apparatus for the thawing of fresh-frozen plasma which does not expose the ports or the contents of the bag to the possibility of contamination.

It is yet another object of the present invention to provide an electromagnetic illuminator for the thawing of frozen plasma which uniformly thaws plasma without overheating localized portions of the plasma.

Another object of the present invention is to provide an electromagnetic illuminator for the quick and hygienic thawing of frozen plasma which avoids microwave "hot" and "cold" spots.

It is yet another object of the present invention to provide an electromagnetic illuminator for thawing frozen plasma which provides a uniform electromagnetic field for thawing the frozen plasma.

It is a further object of the present invention to provide a microwave apparatus for the rapid thawing of frozen plasma which avoids uneven heating of the material begin thawed and which eliminates the possibility of error arising from variations in exposure time according to the volume of material being thawed.

Yet another object of the present invention is to provide an electromagnetic illuminator which quickly, safely, and hygienically thaws frozen plasma.

A still further object of the present invention is to provide an electromagnetic illuminator for thawing frozen plasma which accommodates irregularly-shaped bags.

It is yet another object of the present invention to provide an electromagnetic illuminator which eliminates dielectric discontinuities but which does not thermally insulate the product being thawed so as to aggravate thermal runaway.

Other objects, features, and advantages of the present invention will become apparent upon reading the specification, when taken in conjunction with the drawings and the appended claims.

BRIEF DESCRIPTION OF THE DRAWINGS

FIG. 11 is a schematic view of the electric system of the plasma-thawing apparatus of FIG. 1.

DETAILED DESCRIPTION OF THE DISCLOSED EMBODIMENT

Figure 1:
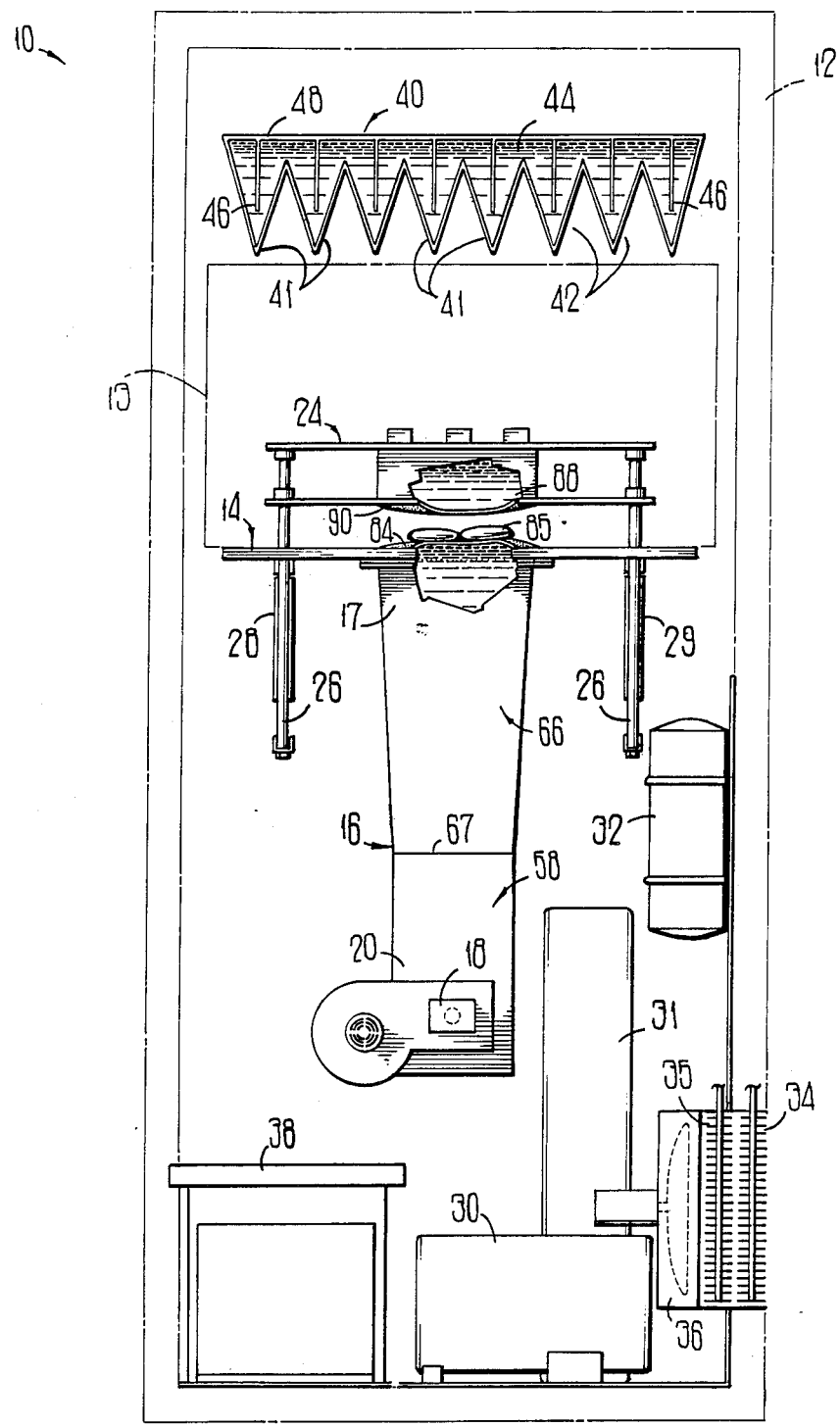
FIG. 1 is an elevational view of a preferred embodiment of a plasma-thawing apparatus according to the present invention.

Referring now to the drawings, in which like numerals indicate like elements throughout the several views, FIG. 1 shows an apparatus 10 for the rapid thawing of cryogenically preserved plasma. The apparatus 10 includes a cabinet 12 comprised of a conductive material, such as steel or other metal, to provide an RF-proof enclosure for safety purposes. In FIG. 1, the front of the cabinet is shown removed to reveal interior detail. However, it will be understood that in the preferred embodiment the cabinet is a complete enclosure with an access door (indicated by the phantom lines 13) provided to afford operational access. Other access doors (not shown) may be provided to permit access to various components for maintenance or repair purposes.

The cabinet 12 has a support frame 14 mounted therein. A waveguide or horn 16 is mounted to the support frame 14 with its open flared end 17 facing upwardly. A magnetron 18 is mounted to the tapered lower end 20 of the horn 16. The construction of the horn 16 and magnetron 18 will be further discussed below with respect to FIGS. 3-5.

A cap assembly 24 is translatably mounted to the support frame 14 above the upper end 17 of the horn 16. The cap assembly 24 is translatably mounted to a set of guide shafts 26. Left and right pneumatic cylinders 28, 29 attached to the support frame 14 raise and lower the cap assembly, as will be explained below with respect to FIG. 2. The purpose, structure, and operation of the cap assembly 24 will be more particularly described hereinbelow with reference to FIG. 6.

Mounted to the wall of the cabinet 12 below the support frame 14 are an air compressor 30, an air tank 31, and a surge tank 32, all of which are components of a pneumatic system for actuating the pneumatic cylinders 28, 29 to lift and lower the cap assembly 24. The operation of the pneumatic system will be more particularly discussed hereinbelow with respect to FIG. 8.

Also mounted in the bottom of the cabinet 12 are an oil cooling radiator 34, a cooling system radiator 35, and a fan 36 for directing a flow of air past the radiators 34, 35. A reservoir/pump subassembly 38 is mounted on the floor of the cabinet 12. The cooling system radiator 35 and reservoir/pump subassembly 38 are in fluid communication with a near field RF absorber 40 located in the top of the cabinet 12 above the cap assembly 24. The cooling system radiator 35, reservoir/pump subassembly 38, and near field RF absorber 40 comprise a cooling system, the operation of which will be more particularly described below with respect to FIG. 6. The oil cooling radiator 34 is a component of an oil cooling system, the operation of which will be described below with respect to FIG. 10.

The near field RF absorber 40 is comprised of a material which is transparent to electromagnetic waves, such as plexiglass. The lower walls 41 of the near field RF absorber 40 comprise of a series of contiguous parallel troughs 42, the walls of which are angled at greater than 45° with respect to horizontal. The near field RF absorber 40 defines a reservoir 44 therein adapted to contain a quantity of water or other suitable liquid for absorbing electromagnetic energy. A plurality of internal baffles 46 depend downwardly from the upper wall 48 of the absorber 40 into the reservoir 44. The lower ends of the baffles 46 are spaced apart from the lower walls 41 of the absorber 40, defining a circuitous path through which a fluid in the reservoir must circulate.

Figure 2:
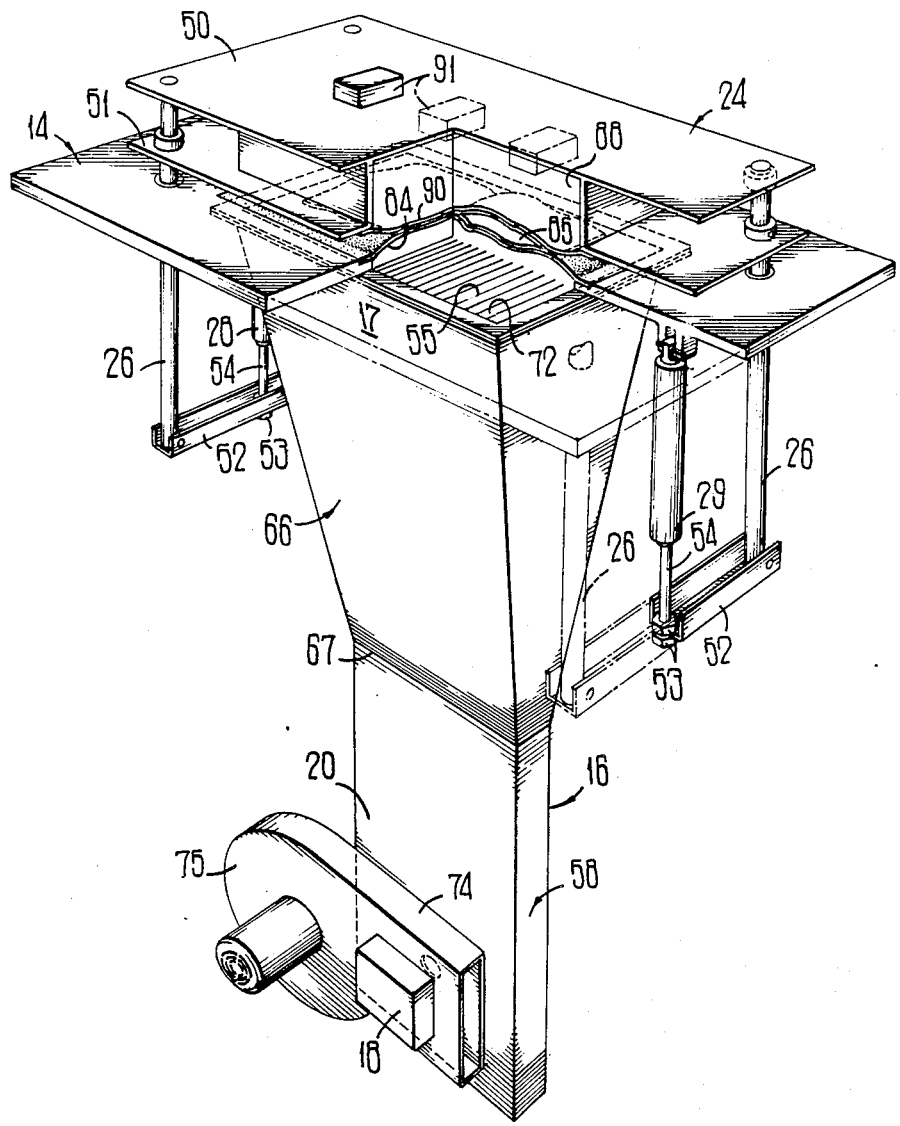
FIG. 2 is a perspective view of the waveguide and cap assembly of the plasma-thawing apparatus of FIG. 1.

Reference is now made to FIG. 2, which more clearly shows the mounting arrangement of the cap assembly 24. As previously indicated, the cap assembly 24 rides on four guide shafts 26, the upper ends of which are secured to upper and lower cap assembly mounting plates 50, 51 and telescopically received through bores in the frame 14. The lower ends of the guide shafts 26 are mounted to either of two brackets 52. The brackets 52, in turn, are mounted to the ends of rods 54 of the left and right pneumatic cylinders 28, 29 respectively. The cylinder rods 54 have threaded ends and are attached to the brackets 52 by means of nuts 53. Adjustment of the height of the brackets 52 is accomplished by appropriate adjustment of the nuts 53 on the threaded ends of the cylinder rods 54.

The cylinders 28, 29 are fixedly mounted beneath the frame 14. As the cylinders 28, 29 are actuated to extend the rods 54, the brackets 52 are displaced downwardly. The cap assembly, linked to the brackets 52 by the guide shafts 26, is thus translated downwardly against the upper end 17 of the horn 16. Conversely, when the cylinders 28, 29 are actuated to retract the rods 54, the brackets 52 are drawn upwardly, forcing the guide shafts 26 upwardly and raising the cap assembly 24 away from the upper end 17 of the horn 16. The mechanics for actuating the cylinders 28, 29 to raise and lower the cap assembly 24 will be explained below with respect to FIG. 8.

Also depicted in FIG. 2, a metal grid 55 is disposed within the aperture 72 in the upper end 17 of the waveguide 16. The structure and function of the metal grid 55 is discussed herein with respect to FIG. 7.

Figure 3:
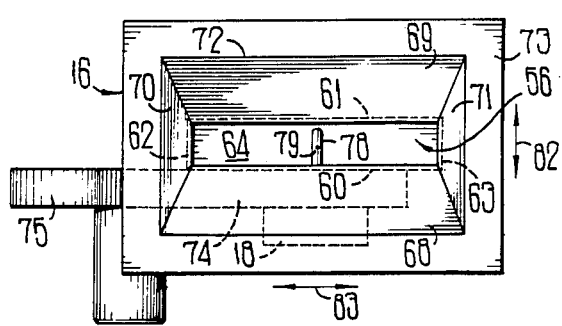
FIG. 3 is a top view of the waveguide of the plasma-thawing apparatus of FIG. 1.
Figure 4:
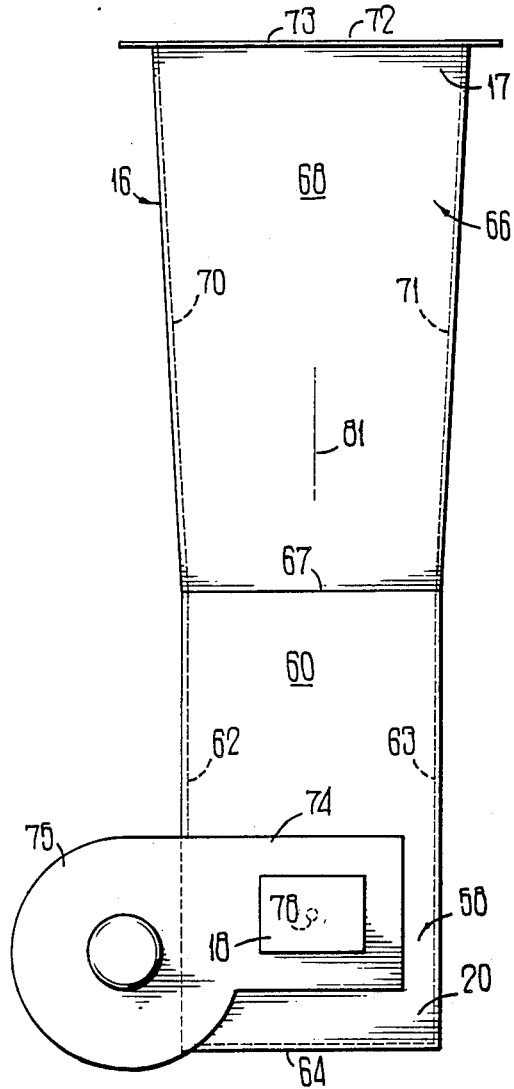
FIG. 4 is a front view of the waveguide of the plasma-thawing apparatus of FIG. 1.
Figure 5:
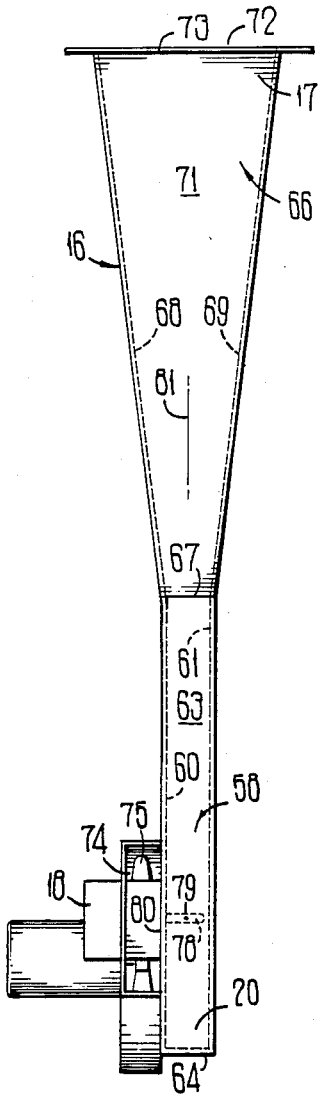
FIG. 5 is a side view of the waveguide of the plasma-thawing apparatus of FIG. 1.

Turning now to FIGS. 3–5, the horn 16 is a hollow waveguide capable of containing RF energy and defining a cavity 56 therein. The horn 16 has a first or lower portion 58 which is rectangular in cross section. First opposing walls 60, 61 and second opposing walls 62, 63 of the lower portion 58 of the horn 16 are generally parallel. The lower portion 58 of the horn 16 of the disclosed embodiment is 1.4 inches by 7.75 inches in cross section and has a length of 18.1 inches. The lower end of the first portion 58 terminates at a backshort 64. The upper end of the first section 58 opens into a second or upper horn section 66 at a juncture 67. This second section 66 has planar walls 68–71 which flare outwardly toward the upper end 17 of the horn 16. The walls 68–17 define rectangular cross sections which increase in area toward the upper end 17 of the horn 16. The horn 16 is open at its upper end 17 at an aperture 72 which in the disclosed embodiment measures 5.6 inches by 9.6 inches. The horn 16 has an outwardly extending peripheral flange 73 at its upper end 17.

As previously stated, the magnetron 18 is mounted adjacent the lower portion 20 of the horn 16. The magnetron 18 of the disclosed embodiment is an 1800 watt commercial magnetron and is selectively operable to generate microwaves within the hollow waveguide 16. The magnetron 18 includes a housing 74 which is bolted to the wall 60 of the lower portion 20 of the waveguide 16. A cooling fan 75 bolted to the magnetron housing 74 directs a flow of air through the magnetron housing to cool the magnetron.

The probe or antenna 78 of the magnetron 18 is disposed within the first horn section 58. The maximum radiation point 79 of the magnetron 18 of the disclosed embodiment is located 1.21 inches from the mounting face 80 of the magnetron, and the magnetron is mounted such that this maximum radiation point is located at the center of the cross section of the lower section 58 of the hollow waveguide 16. The horn 16 confines and guides the waves generated by the magnetron 18 along an axis of propagation coincident to the longitudinal axis of the horn (indicated by the line 81 in FIG. 5).

The object of the horn 16 is to provide an electromagnetic field of substantially uniform intensity across the horn aperture 72. As will be appreciated by those skilled in the art, a waveguide will typically support several harmonic modes of wave propagation. Single-mode operation provides nonuniform power density across the cross section of the waveguide. Multiple harmonic mode operation, or "multimode" operation, which is to be avoided in most waveguide applications, is used in the present invention to provide a more uniform power density across the cross section of the waveguide at a desired location along the axis of propagation. Even-numbered harmonic transverse electric field modes produce a nununiform power density across the cross section of the waveguide. In the preferred embodiment the horn is configured to propagate only odd-numbered transverse electric field modes, e.g. first, third, and fifth modes of propagation, to produce a more uniform power density across the aperture. To encourage generation and propagation of only odd-numbered modes, the first or lower portion 58 of the horn 16 of the disclosed embodiment is relatively narrow in the E-field direction (indicated by the arrow 82 in FIG. 3). The cumulative effect of the multiple odd-numbered electric field modes of propagation creates an electromagnetic field of substantially uniform intensity across the horn aperture 72 in the direction of electromagnetic intensity of the microwaves, i.e. in the H-field direction (indicated by the arrow 83). The design and selection of a horn to achieve this objective is well within the ordinary level of skill in the art and will thus be described only broadly.

The length of the horn 16 of the disclosed embodiment is selected by first choosing a length at which the first, third, and fifth modes are in phase. In the disclosed embodiment, the length of the horn thus selected measures 30.8 inches from the backshort 64 to the aperture 72. Next, the location of the magnetron probe 78 is spaced from the backshort 64 at a distance at which the first, third, and fifth harmonic modes are in phase. It will be appreciated that there are several points along the axis of propagation 81 which will meet this phasing requirement. However, a point should be selected which is at least one wavelength from the juncture 67 of the first and second horn sections 58, 66, that is, from the point at which the horn 16 begins to flare. The one wavelength requirement assists in the generation and propagation of the modes described above. As will be further appreciated by those skilled in the art, the spacing between the probe 78 and the backshort 64 also determines the relative power assigned to the various modes of propagation. In the preferred embodiment, the magnetron probe 78 is located 3.85 inches from the backshort 64.

Figure 6:
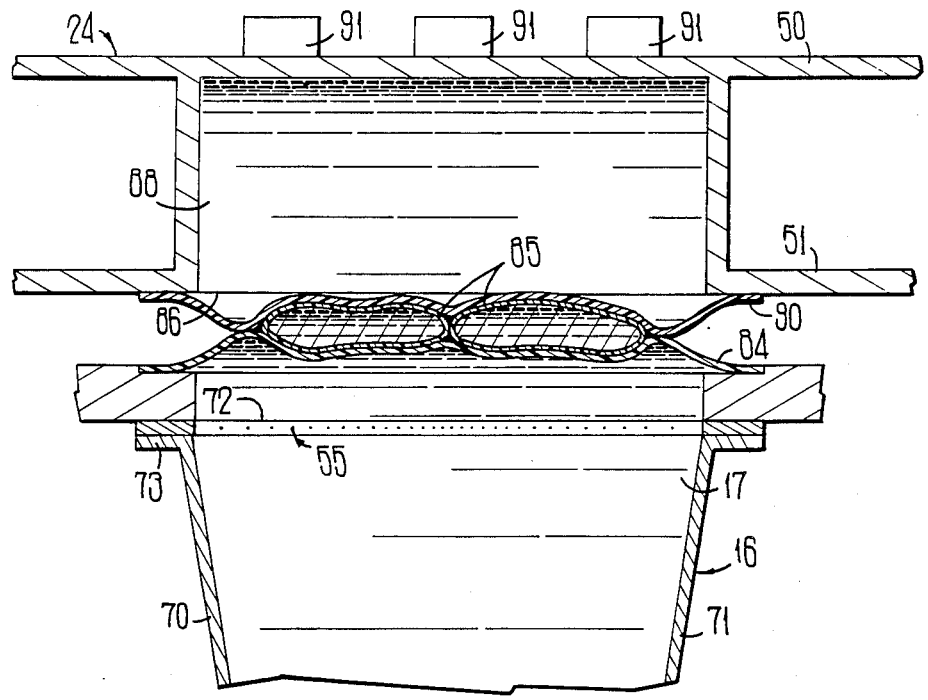
FIG. 6 is a partial side cut-away view of the plasma-thawing apparatus of FIG. 1 showing the cap assembly lowered against the upper end of the waveguide.

Referring now to FIG. 6, mounted within the aperture 72 at the top of the waveguide 16 is the metal grid 55. Disposed across the aperture 72 just above the grid 55 is a membrane 84. The membrane is comprised of a flexible material having a dielectric constant substantially equal to the dielectric constant of frozen plasma, i.e., 2.7. In the disclosed embodiment, the membrane is approximately 0.007 inches in thickness and is comprised of a flexible polyvinyl chloride material. The membrane 84 completely covers the upper end 17 of the horn 16 and is sealed watertight around its edges. As will be seen, the membrane 84 serves two purposes: sealing the horn and providing a support surface for supporting up to two bags of frozen plasma 85 at the aperture 72 of the waveguide 16.

The cap assembly 24 is open at its lower end 86 and defines a cavity 88 therein. The lower end 86 of the cap assembly 24 has a size and shape substantially corresponding to the size and shape of the upper end 17 of the horn 16. As previously disclosed, the cap assembly 24 is mounted so that it can be translated to engage the lower end 86 of the cap assembly against the upper end 17 of the horn 16. A flexible membrane 90, similar to the flexible membrane 86 mounted across the aperture 72 of the waveguide 16 and comprised of the same flexible PVC material, covers the opening at the bottom of the cap cavity 88. The seal between the flexible membrane 90 and the cap assembly 24 is watertight so that the cavity 88 is capable of containing a liquid therein. A series of fiber optic sensors 91 are mounted in the top of the cap assembly 24 scanning downwardly. The operation of the fiber optic sensors 91 will be described more particularly below.

Figure 7:
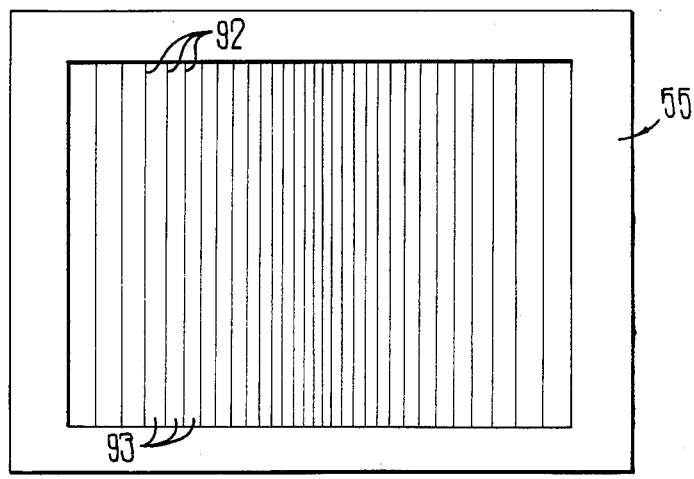
FIG. 7 is a plan view of the energy redistribution grid of the plasma-thawing apparatus of FIG. 1.

FIG. 7 shows the metal grid 55 which is disposed in the upper end 17 of the waveguide 16 proximate the aperture 72. The metal grid 55 functions to redistribute the electromagnetic wave pattern at the aperture 72 of the waveguide 16. At lower magnetron power settings, e.g. 500–600 watts, the energy distribution afforded by the additive effects of the multiple odd-numbered harmonic modes is substantially uniform across the aperture 72. However, at higher power settings, variations in the power distribution across the aperture are amplified and become more pronounced. Thus, at high power settings, the electromagnetic wave pattern must be "fine tuned" to eliminate such variations.

The metal grid 55 serves to redistribute the wave pattern by providing a plurality of conductive elements 92 defining a plurality of slots 93 therebetween. The conductive elements 92 are disposed at areas of peak power, reflecting the microwave energy incident on the slots 93. Thus, energy intensity at "peak" locations is attenuated, and the energy distribution across the aperture is rendered more uniform.

In the disclosed embodiment, the grid 55 is comprised of a circuit board printed on a phenolic plastic having a dielectric constant of about 2.7. The plurality of slots 93 are formed by etching off the conductive coating of the circuit board, leaving the conductive coating in place to form the conductive elements 92. As will be appreciated, the amount and locations of energy passing through the grid 55 can be controlled by controlling either the spacing between adjacent conductive elements 92 or the width of the conductive elements, or some combination of the two. In the disclosed embodiment, the conductive elements 92 are spaced more closely together toward the center of the grid, where the power distribution afforded by the waveguide 16 tends to be highest. To permit the flow of fluid through the grid 55 to maintain pressure on the membrane 84, a plurality of apertures may be formed in the circuit board comprising the grid.

Another method of forming the metal grid is to attach a number of parallel metal wires to a rectangular frame. The metal wires thus comprise the conductive elements, and the spaces between the wires comprise the plurality of slots. The microwave energy incident on the wires will be reflected, while the remainder of the energy will pass through the spaces between the wires.

Figure 8:
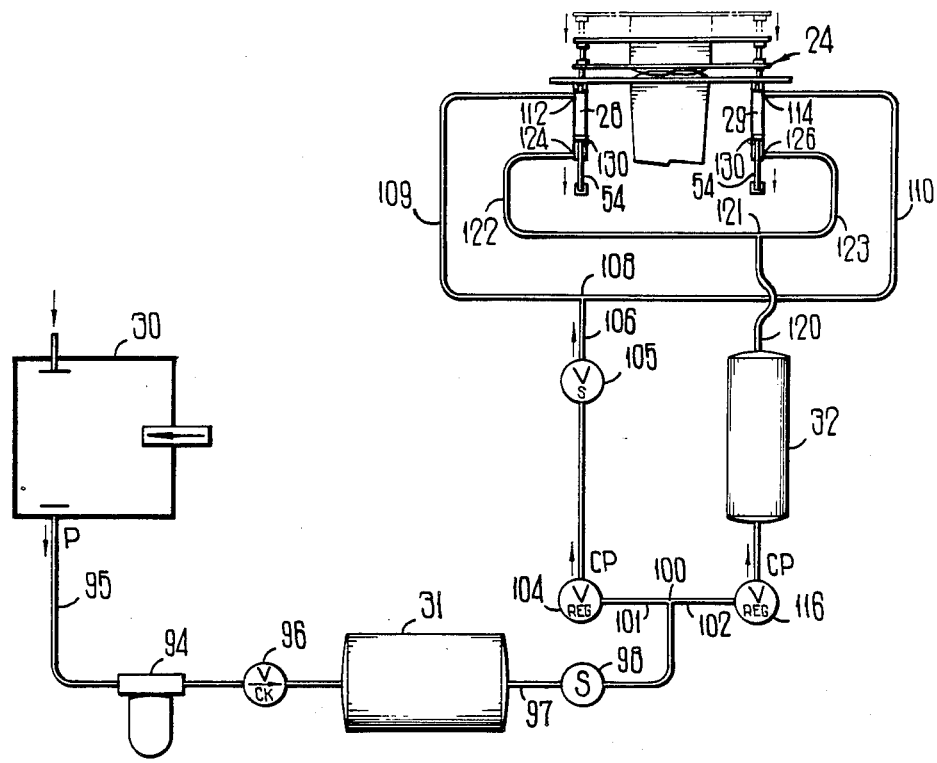
FIG. 8 is a schematic view of the pneumatic system of the plasma-thawing apparatus of FIG. 1.

FIG. 8 is a schematic diagram of a pneumatic system for lifting and lowering the cap assembly 24. The pneumatic system includes the air compressor 30 for generating a supply of compressed air to the air tank 31, both of which components were previously depicted in FIG. 1. A moisture trap 94 is located in a line 95 between the air compressor 30 and the air tank 31 to capture condensation caused by the compression of the air. Also in line between the compressor 30 and the air tank 31 is a check/unloader valve 96. The check/unloader valve 96 opens when the air compressor 30 is first started to vent the line 95 to the ambient. With the line 95 vented, the air compressor 30 is thus not subjected to a load. Once the compressor 30 has reached operating speed, the check/unloader valve 96 closes to direct the compressed air into the air tank 31. By thus relieving the load from the air compressor 30 as it is being started, it is possible to use a smaller compressor motor than would be required if the compressor were forced to start under load.

In the line 97 leaving the air tank 31 is a pressure switch 98 which switches the compressor 30 on and off to maintain the proper pressure in the air tank. In the disclosed embodiment, the pressure switch 98 turns the compressor 30 on when the pressure in the tank 31 is less than 75 psi and turns the compressor off when the pressure in the tank reaches 85 psi. In this manner, the pressure switch 98 operates to maintain a pressure in the tank 31 of 75–85 psi.

Downline from the pressure switch 98 is a T-junction 100 which splits the single line 97 into left and right branches 101, 102. The left branch 101 includes an in-line regulator valve 104 set to provide a line pressure of 30 psi. Downline from the regulator valve 104 is a solenoid valve 105 which is normally closed and which opens under power. When the solenoid valve 105 is closed, air pressure in the left branch 101 is exhausted to the ambient. When the solenoid valve 105 is powered, the exhaust closes and the line 106 beyond the solenoid valve 105 is pressurized. The left branch 101 further splits at a junction 108 into two hoses 109, 110, the hose 109 going to the upper port 112 of the left cylinder 28, and the hose 110 going to the upper port 114 of the right cylinder 29.

The right branch 102 includes an in-line regulator valve 116 for maintaining the pressure in the right branch at 11 psi. Downline of the regulator valve 116 is the surge tank 32, previously depicted in FIG. 1. A line 120 coming out the surge tank 32 splits at a junction 121 into two hoses 122, 123. The hose 122 goes to the lower port 124 of the left cylinder 28, and the hose 123 goes to the lower port 126 of the right cylinder 29.

It will be appreciated that the right branch 102, and hence the lower ports 124, 126 of the left and right cylinders 28, 29 are always pressurized at 11 psi. When the solenoid valve 105 is not powered, the air pressure in the left branch 101 is being exhausted, and the upper ports 112, 114 of the left and right cylinders 28, 29 are not under pressure. Thus, the 11 psi of pressure being exerted in the right branch 102 to the lower ports 124, 126 of the cylinders 28, 29 forces the pistons 130 upwardly, retracting the rods 54 and lifting the cap assembly 24 to a raised position. When the solenoid valve 105 is powered, the left branch 101, and hence the upper ports 112, 114 of the cylinders 28, 29 is pressurized at 30 psi, which is sufficient to overcome the 11 psi pressure on the lower side of the pistons 130 and to displace the pistons downwardly, extending the rods 54 and lowering the cap assembly 24. As the pistons 130 are displaced downwardly, the air in the lower portion of the cylinders 28, 29 is displaced back down the hoses 122, 123 into the surge tank 118.

The design of the pneumatic system provides the feature that the solenoid valve 105 must be powered to keep the left branch 101 pressurized. The advantage of this feature is that if the system experiences a power failure the solenoid valve 105 will automatically close, exhausting the pressure in the left branch 101. Even with the air compressor 30 not operating, the reservoir of pressurized air in the surge tank 32 is sufficient to pressurize the right branch 102 to return the cap assembly 24 to its raised position. The cap assembly 24 thus defaults to a raised position in the event of a pneumatic system failure.

Figure 9:
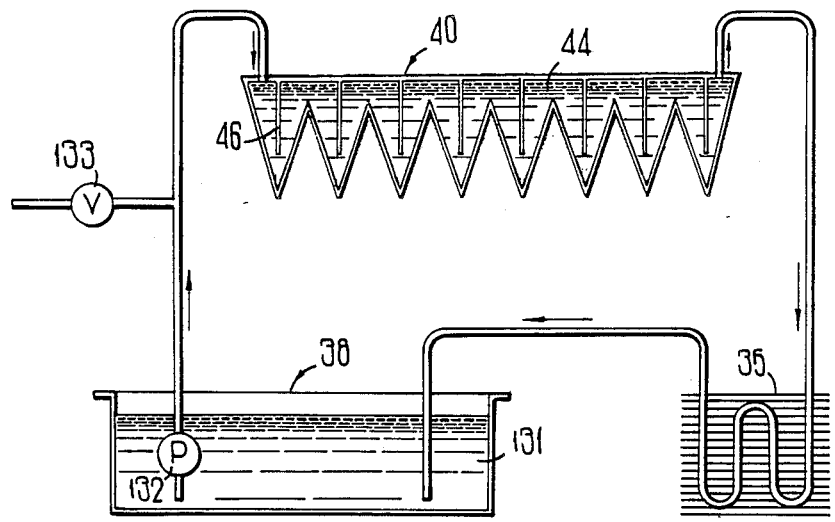
FIG. 9 is a schematic view of the RF absorber cooling system of the plasma-thawing apparatus of FIG. 1.

FIG. 9 is a schematic diagram of a cooling system for cooling the water in the near field RF absorber 40. Water circulates around the baffles 46 in the absorber reservoir 44, absorbing any microwave energy which reaches the absorber. The water is then pumped out of the absorber to the cooling system radiator 35, where the flow of air drawn over the radiator by the fan 36 dissipates the heat and cools the water. The cooled water is then pumped to a sump 131 in the reservoir/pump subassembly 38. Water from the sump 131 is then pumped back to the RF absorber 40 by a pump 132. The pump 132 of the disclosed embodiment circulates water through the cooling system at a rate of three gallons per minute. The cooling system also includes a fill/dump valve 133, which valve is normally closed but can be opened to add or withdraw water from the cooling system.

Figure 10:
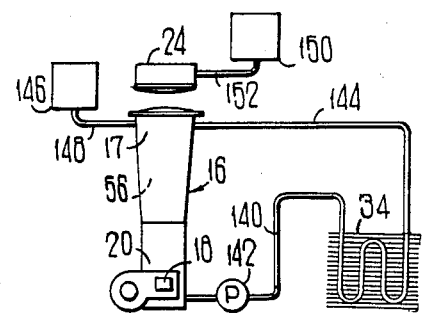
FIG. 10 is a flow diagram of the dielectric oil loading the waveguide and cap of the plasma-thawing apparatus of FIG. 1.

FIG. 10 is a flow diagram for a liquid dielectric material loading the waveguide 16 and cap assembly 24. The interior 56 of the hollow waveguide 16 is filled with an oil having a dielectric constant substantially equal to the dielectric constant of frozen plasma, i.e., 2.7. In the disclosed embodiment, the dielectric oil is a silicon oil and is known in the industry under the terms "transformer oil" and "klystron oil". The dielectric oil is substantially transparent to the electromagnetic waves propagating through the horn 16 and thus is not heated by the microwave energy. However, the dielectric oil serves as a "heat sink" for heat generated by the magnetron 18 and is conductively heated thereby. Since the flexible membrane covering the aperture 72 of the horn is subject to deformation if heated much above 100° F., the dielectric oil must be cooled to dissipate the heat absorbed from the magnetron.

As seen in FIG. 10, oil is withdrawn from the waveguide 16 through a line 140 at the lower end 20 of the horn. A pump 142 in the line 140 circulates the oil through the radiator 34. As shown in FIG. 1, air is drawn through the radiator 34 by the fan 36 to cool the oil as it circulates therethrough. The radiator 34 and fan 36 have previously been disclosed with respect to FIG. 1. The cooled oil is then returned to the upper end 17 of the horn 16 through a line 144.

The cap assembly 24 is similarly charged with the dielectric oil. However, since the oil in the cap assembly 24 is thermally uncoupled from the magnetron 18, the oil in the cap assembly is not conductively heated by the magnetron. Thus, unlike the oil in the waveguide 16, the oil in the cap assembly 24 need not be cooled.

As is also depicted in FIG. 10, a horn oil reservoir 146 is disposed slightly above the upper end 17 of the horn 16 and is in fluid communication with the horn by a line 148. Similarly, a cap oil reservoir 150 is disposed slightly above the cap assembly 24 and is in fluid communication with the cap assembly by a line 152. The upper ends of both reservoirs 146, 150 are open to the ambient. Gravitational forces acting on the oil in the reservoirs 146, 150 exerts a positive fluid pressure through the lines 148, 152 which exerts a pressure on the flexible membranes 84, 90, to the advantage hereinbelow described. The amount of pressure on the membranes 84, 90 can be controlled by controlling the volume of oil in the reservoirs 146, 150.

FIG. 11 is a schematic diagram of the electrical system of the preferred embodiment of the present invention. The preferred embodiment is powered by 220–240 VAC which is brought in via power conductors 160 and 161 and a neutral conductor 162. The conductors 160 and 161 are fused by 20 amp fuses ad 163 and 164, respectively, and then become conductors 165 and 166, respectively. The conductor 165 is connected to a bus block 168 through the parallel combination of a normally open test switch 169 and the normally open contacts of a relay 170. A bus block 176 is connected to the neutral conductor 162 through a 10 amp fuse 177. A magnetron cooling blower motor 172 for driving the cooling fan 75, an absorber/oil cooling blower motor 173 for driving the fan 36, a water coolant pump motor 174 for driving the pump 32, and an oil coolant pump motor 175 for driving the pump 142 are connected in parallel between the bus block 168 and the bus block 176. In the preferred embodiment, motors 172–175 are rated for 110 VAC operation. The motors 172–175 operate whenever the test switch 169 is closed or when the relay 170 is energized. An air compressor motor 180, in series with the air switch 98, is connected between the neutral conductor 162 and the fuse conductor 166 and drives the air compressor 30. The compressor motor 180 is also rated for 110 VAC operation and operates whenever the air switch 98 is closed. The operation of motors 172–175, compressor motor 180, and air switch 98 has been previously described.

The primary 182a of a transformer 182, in series with a magnetron thermal protect breaker 183, is connected between the neutral conductor 162 and the fuse conductor 165. The two secondaries 182b, 182i c of the transformer 182 provide power to a controller 184. In the preferred embodiment, the transformer 182 is a Keystone transformer number 45507, and the controller 184 is a Litton controller, drawing number D-0500000101, Revision A. If the magnetron 18 begins to overheat, a breaker 183 interrupts power to the transformer 182, thereby temporarily disabling the controller 184.

Signal input pins 1 and 2 of the controller 184 are connected by conductors 186 and 187, respectively, to a normally opened switch 185a. The switch 185a is part of an interlock switch module, such as Litton, Drawing No. 45585A. When door 13 is opened, switches 185a and 185d close and switches 185b and 185c open. Output pins 3 and 4 of the controller 184 are connected by conductors 200 and 201, respectively, to the coil of the relay 170. Output pin 7 of the controller 184 is connected by a conductor 202 to the control input of temperature control 192. Output pin 8 of the controller 184 and the output of the temperature control 192 are connected by a conductors 203 and 204, respectively, to the inputs of an isolated coupler triac circuit 193. The temperature control 192 acts as a safety device for the magnetron 18. In the preferred embodiment, the temperature control 192 is a Spectralogic, Inc. Part No. LBLD001. The temperature control 192 first checks the bag color through the use of light sensitive diodes operating via fiber optics and then checks the bag temperature through the use of an Advanced Fiber Optics, Inc. infrared fiber optic temperature sensor. If the sensors detect that the bag color is dark, indicating that blood, rather than plasma, has been loaded into the apparatus, the triac will not fire. If the sensors detect that the bag color is light, i.e. not blood, the infrared fiber optic sensor detects the initial bag temperature, and the microprocessor then sets the thaw time based on that initial bag temperature. As thawing continues, the microprocessor monitors bag temperature through the infrared fiber optic sensors and shuts down the magnetron when the bag temperature reaches 30° C.

The conductor 165 is also connected through normally open contacts of a relay 191 and the normally open contacts of a switch 185c to a conductor 205, which is connected to one of the output terminals of the triac 193 and to the primary 207a, being connected between the conductors 205 and 166, has an input voltage of 220–240 VAC. The conductor 205 is also connected through a switch 185d to the conductor 166.

Switches 185c and 185d, in conjunction with the contacts of the relay 191 and the fuses 163 and 164, form a safety interlock which disables the device in the event that the access door 13 is opened, the switch 185c fails in the closed position, and any condition occurs which causes the contacts of the relay 191 to remain closed. When the door 13 is opened, switch 185d closes, so that if switch 185c has failed closed and the contacts of relay 191 have remained closed, a short will appear between the conductors 165 and 166, thereby blowing the fuse 163 or fuse 164, or both, interrupting the power to the transformer 207 and terminating the generation of microwave radiation. The opening of the door 13 closes the switch 185a and opens the switches 185b, 185c. The closing of the switch 185a causes the controller 184 to de-energize the relay 170. The opening of the switch 185b de-energizes the relay 191 and the temperature control 192. The opening of the switch 185c removes power from the triac 193 and the transformer 207. Also, the de-energizing of the relay 191 will remove power from the triac 193 and the transformer 207. Thus, the interlock switch module 185 serves to assure that if the door is opened microwave generation and radiation is immediately terminated.

The other power terminal of the triac 193 is connected by a conductor 206 to the primary 220a of a transformer 220. The primary 220a is connected to the 110 VAC conductor 196 through a transformer thermal protect breaker 191. If the transformer 220 begins to overheat, then the breaker 191 opens up and removes power from the transformer 220. The transformer 207 and the transformer 220 each have two secondary windings, 207b, 207c, and 220b, 220c, respectively. The transformer 207 is a commercial filament transformer, and the transformer 220 is a commercial filament and high voltage transformer. A 4 microfarad, 600 volt capacitor 210 is connected across the secondary winding 207c of the transformer 207. One end of the secondary winding 207c is connected to the neutral conductor 162. The secondary winding 207c, in conjunction with the capacitor 210, reduces the amount of noise generated and placed on the lines 160 and 161.

One end of the secondary winding 207b is connected by a conductor 213 to one end of the filament of the magnetron 18. The other end of the winding 207b is connected by a conductor 212 to one end of the secondary winding 220b of the transformer 220. The other end of the secondary winding 220b is connected by a conductor 217 to the other end of the filament of the magnetron 18, to the anode of a diode 215, and to one end of a capacitor 216. One end of the high voltage secondary winding 220c is connected to the anode of a diode 193 and the cathode of the diode 215. The other end of the winding 220c is connected by a conductor 192 to the other end of the capacitor 216 and to one end of a capacitor 194. The other end of the capacitor 194 and the cathode of the diode 193 are connected to the neutral conductor 162. The anode of the magnetron 18 is also connected to the neutral conductor 162. The diodes 215 and 223 are HVPR 10-14 8350 rectifiers, rated at 6 kilovolts and 650 milliamps. The capacitors 216 and 194 are rated at 9400 microfarads and 2500 volts. It will be appreciated that the diode 215 and the capacitor 216 form a halfwave rectifier and that the diode 193 and the capacitor 194 also form a halfwave rectifier. Each halfwave rectifier operates independently of the other. They are connected in series to form a voltage doubler to provide operating power for the magnetron 18.

It should be noted that the transformer 207 receives the full 220 volts present between the conductors 165 and 166. However, the triac 193, in a conventional manner, applies or removes operating voltage for the transformer 220. Therefore, depending upon the controller 184 and temperature control 192, transformer 220 may receive the full 220 volts or no operating voltage. Typically, when the magnetron is providing a radio frequency output power, the filament power to the magnetron is decreased to prevent the filament from overheating and burning through. Therefore, the secondary windings 207b and 220b of the transformers 207, 220 are connected in opposition so that, when the triac 193 is providing operating power to the transformer 220, the filament voltage provided by the secondary winding 207b is reduced by the opposition voltage provided by the secondary winding 220b. However, when the triac 193 is not providing operating power to the transformer 220, then the opposition voltage provided by the secondary 220b will be zero, and the filament of the magnetron 18 will receive the full voltage of the secondary 207b. Also, to assure that the filament is properly heated, the controller 184 causes power to be applied to the filament transformer 207 about ½ second before power is applied to the transformer 220.

Referring now to the operation of the apparatus 10, a bag of frozen plasma 85 is paced on the upper surface of the membrane 84 atop the horn 16. When the operator closes the door 13 and actuates the relay 170, the fiber optic sensors 91 in the cap 24 first sense whether the object on the membrane 16 is a dark color. If so, the sensors 91 send a signal to the control unit 184, which determines that the substance on the membrane 84 is not plasma, and the unit will not operate. If the sensors 92 detect no dark substance on the membrane 84, the operation commences.

The pneumatic system is then actuated. The control unit 184 sends a signal t close the solenoid valve 105 and pressurize the upper ports 112, 114 of the cylinders 28, 29. The pressure on the upper surface of the pistons 130 is sufficient to displace the pistons downwardly, extending the rods 54 and lowering the cap assembly 24 against the upper end 17 of the horn 16. If at any time the pressure switch 98 senses that the pressure in the air tank 31 is less than 75 psi, the compressor 30 is started. The check/unloader valve 96 first opens to vent the line 95 to the ambient, thereby removing the load from the compressor 30 and facilitating startup. When the compressor 30 has reached operating speed, the check/unloader valve 96 is closed, directing the supply of compressed air to the tank 31. When the pressure switch 98 detects that the pressure in the air tank 31 has reached 85 psi, the compressor is shut down.

As the cap assembly 24 is rapidly lowered against the upper end 17 of the horn 16, the flexible membrane 90 on the lower end 86 of the cap assembly contacts the upper surface of the bag 85 of frozen plasma. The opposing lower surface of the bag 85 is thereby forced downwardly against the horn membrane 84. In turn, the horn membrane 84 is displaced downwardly, and a corresponding volume of the dielectric oil loading the horn 16 tends to be displaced out of the cavity 156 of the horn and into the horn oil reservoir 146. However, the high viscosity of the dielectric oil in the horn prevents the oil from being displaced rapidly, thereby maintaining an upward pressure on the horn membrane 84 and forcing the membrane to conform intimately to the lower surface of the bag 85.

The resistance of the horn membrane 84 to the downward force of the cap member 24 causes the plasma bag 85 to exert an opposing upward force against the cap membrane 90. As the upper surface of the plasma bag 85 is forced against the cap membrane 90, the cap membrane is displaced upwardly. A corresponding volume of the dielectric oil in the cavity 88 of the cap assembly 24 thus tends to be displaced out of the cavity and into the reservoir 150. Again, however, the high viscosity of the liquid dielectric prevents its rapid displacement from the cavity 88, thereby maintaining a downward pressure on the cap membrane 90 which forces the cap membrane to intimately conform to the upper surface of the plasma bag 85.

With the cap assembly 24 thus lowered, the plasma bag 85 is intimately surrounded by the membranes 84, 90 on all sides, and air pockets which can cause dielectric discontinuities are eliminated. The flexibility of the membranes 84, 90 and the pressure exerted by the dielectric oil are such that the membranes will intimately conform to even badly misconfigured plasma bags, such as occur when the plasma bag is frozen in an irregular shape.

When the cap assembly 24 is lowered and the plasma bag 85 is encapsulated by the membranes 84, 90, the magnetron 18 is actuated. Electromagnetic waves travel upwardly through the dielectric oil in the horn 16 and are spread by the horn across its cross-sectional area. The configuration of the waveguide 16 supports the first, third, and fifth harmonic modes of wave propagation, the additive effect of which modes creates an electromagnetic field of substantially uniform intensity across the waveguide aperture 72. The field is "fine-tuned" by the grid 55 disposed just below the aperture, as microwaves incident on the conductive elements 92 of the grid are reflected, and waves incident on the slots 93 are passed through the grid. The bags 85 of plasma supported on the horn diaphragm 84 are thus subjected to a magnetic field which is substantially uniform in the direction of electromagnetic intensity of the microwaves. "Hot spots," or areas of nonuniform electromagnetic illumination, are thereby substantially eliminated.

Since the liquid dielectric material loading the horn 16 has the same dielectric properties as the horn membrane 84, no dielectric discontinuity is created at the interface between the liquid dielectric and the lower surface of the membrane. Also, the plasma bag 85, comprised of polyvinyl chloride, has similar dielectric properties to the horn membrane 84, so no dielectric discontinuity exists at that interface. In a like manner, the frozen plasma in the bag 85, the cap membrane 90, and the liquid dielectric medium in the cavity 88 of the cap assembly 24 all share similar dielectric properties, such that there are no dielectric discontinuities at any location between the magnetron 18 and the upper end of the cap assembly 24 which could cause reflection of the microwaves and thereby disrupt the energy distribution.

The portion of the microwave energy which is not absorbed by the plasma and propagates through the bags 85 will encounter the upper end of the cap assembly 24. Since the upper end of the cap assembly is comprised of a material which is transparent to microwaves, the majority of the electromagnetic waves will propagate through the upper end of the cap assembly. However, because of the interface with the air at the upper end of the cap assembly, which is an interface between materials of differing dielectric properties, a certain percentage of the microwaves will be reflected downwardly back into the cap assembly. In the disclosed embodiment, it is estimated that approximately 50% of the electromagnetic energy will pass through the plasma bags 85, and that approximately 15% of that energy, or 7.5% of the energy incident on the lower surface of the plasma bags, will be reflected back into the cap assembly 24. To accommodate this reflected energy, the upper end of the cap assembly 24 is located in integer number of wavelengths plus $\frac{1}{4}$ or $\frac{3}{4}$ wavelength from the magnetron. In this manner, the waves reflected from the upper end of the cap assembly will be in phase with the incident waves. It will further be appreciated that approximately 50% of the reflected energy will be absorbed by the plasma on its return pass through the bags 85, such that only approximately 3.75% of the generated microwave energy is passed back into the horn 16. This amount of reflected energy is sufficiently minimal that overheating of the magnetron 18 is unlikely.

Microwaves which propagate through the upper end of the cap assembly 24 strike the near field RF absorber 40 in the upper end of the cabinet 12. Most of the incident electromagnetic waves pass through the plexiglass lower walls 41 of the absorber and into the reservoir 44. The few reflected waves, because of the angle of the lower walls 41 of the lower surface of the absorber, are reflected to another wall of the lower surface of the RF absorber, and most of the reflected waves pass through the second wall into the reservoir 44. Only a fractional quantity of the incident electromagnetic waves are reflected off the second wall. The vast majority of the electromagnetic energy thus passes into the reservoir 44, where it is absorbed by the water.

The water in the near field RF absorber 40 is heated as it absorbs the electromagnetic energy. To dissipate the heat, the water is circulated to the radiator 35, where air drawn past the radiator by the cooling fan 36 cools the water. The cooled water then circulates to the sump 131 and thence back to the RF absorber 40.

As the plasma in the bags 85 begins to thaw from the microwave illumination and changes from a solid into a liquid state, the dielectric properties of the plasma change radically. The dielectric constant of the liquid plasma is many times higher than that of frozen plasma, such that the plasma absorbs energy at a higher rate and heats much faster. However, since the entire volume of plasma is illuminated substantially uniformly, the problem of isolated portions of the plasma liquefying rapidly and thermally "running away" from the surrounding frozen plasma is greatly attenuated. Further, the present invention provides the advantage that the plasma bags are intimately surrounded by the dielectric oil, which serves as a thermal damper and thereby greatly impedes the thermal runaway phenomenon.

When the appropriate amount of heating time has passed, the control circuitry turns off the magnetron 18. The current powering the solenoid valve 105 is turned off, and the valve opens to vent the left branch 101 of the pneumatic circuit to the ambient. The pressure in the right branch 102 is thereby sufficient to force the pistons 130 of the pneumatic cylinders 28, 29 upwardly, retracting the rods 54 and raising the cap assembly 24 away from the upper end 17 of the horn 16. The bag 85 of thawed plasma can now be removed from the unit.

Figure 12:
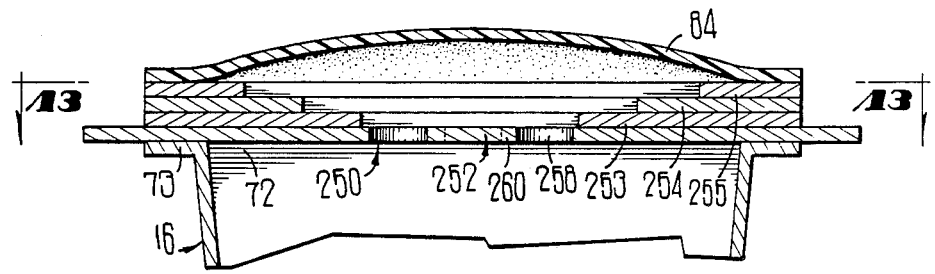
FIG. 12 is a side cut-away view of a dielectric lens assembly of a first alternate embodiment of a plasma-thawing apparatus according to the present invention.
Figure 13:
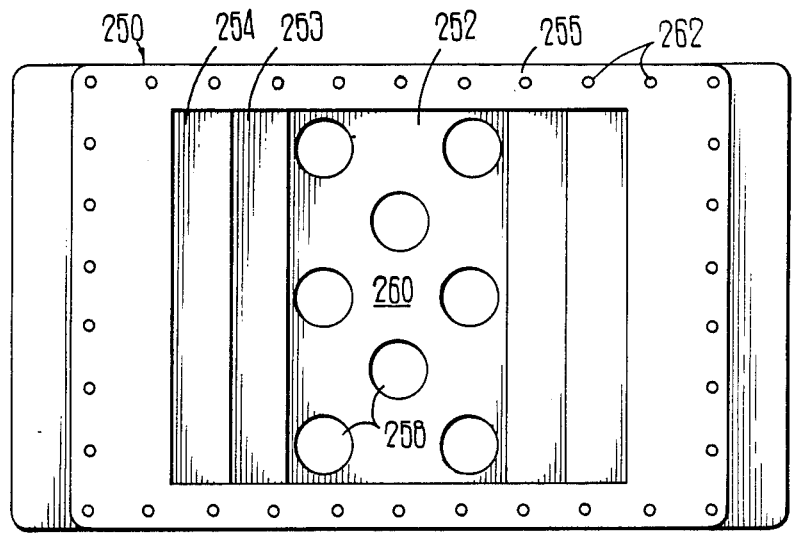
FIG. 13 is a cutaway view of the dielectric lens assembly taken along line 13—13 of FIG. 12.

In an alternate embodiment of the invention, FIGS. 12-13 disclose a differential dielectric lens assembly 250 which may be used in place of the metal grid 55 for redistributing the electromagnetic field at the aperture 72 of the horn 16. The lens assembly 250 comprises a support sheet 252, a bottom lens sheet 253, a middle lens sheet 254, and a top lens sheet 255 all laminated in superimposed relation. All four sheets 252-255 are comprised of a rigid polyvinyl chloride material. The support sheet 252 fits directly against the flange 73 of the RF horn 16 and is sized to cover the aperture 72 of the horn. The support sheet 252 has a number of holes 258 formed in this central portion 260 to permit the dielectric oil loading the waveguide to flow therethrough.

The exterior dimensions of the three lens sheets 253-255 substantially correspond to the exterior dimensions of the horn flange 73. The bottom sheet 253 has a rectangular opening formed in its central portion. The middle sheet 254 has a somewhat larger rectangular opening formed in its central portion, and the top sheet 255 has an even larger rectangular opening formed in its central portion. The effect of the different sized rectangular openings is that the lens assembly 250 is four sheets in thickness at its periphery, graduating to only a single sheet in thickness in its central portion. The top, middle and bottom lens sheets 253-255 each have a high-dielectric coating on their upper and lower surface. Such high dielectric sheets are well known in the industry and are available from a number of manufacturers. The coating on the lens sheets 252-255 of the alternate embodiment has a dielectric constant of about 30. All four sheets 252-255 have a plurality of corresponding coaxial holes 262 formed around their perimeters whereby the sheets may be bolted to the flange 73 of the horn 16. With the lens assembly 250 thus mounted to the flange 73 of the waveguide, the horn membrane 84 is mounted onto the top lens 255.

The differential dielectric lens assembly 250 distributes the electromagnetic field across the aperture of the waveguide in much the same manner as an optical lens distributes light. At each lens surface, the dielectric differential between the polyvinyl chloride sheet material and the coating medium on the surface of the lenses 253-255 refracts the electromagnetic waves. The resulting energy distribution is substantially uniform across the broad central portion of the horn aperture and drops off sharply at the periphery of the horn.

Figure 14:
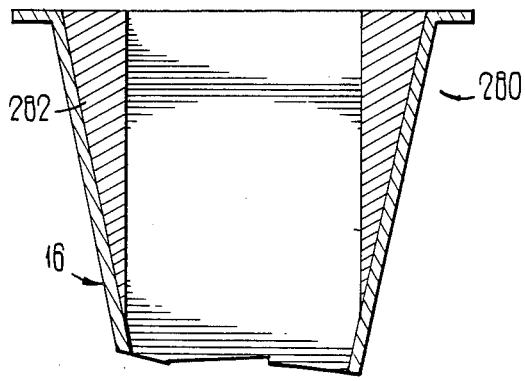
FIG. 14 is a side cut-away view of the upper portion of the waveguide of a second alternate embodiment of a plasma-thawing apparatus according to the present invention.

A second alternate embodiment 280 of the invention is disclosed in FIG. 14. In this embodiment, the lateral edges of the waveguide 16 are loaded with a material 282 having a high dielectric constant to redistribute the electromagnetic field. In the disclosed embodiment, the loading material is manufactured by Emerson & Cumming under the trademark "Eccoflo" and has a dielectric constant of about 16. The electromagnetic waves at the outer edges of the waveguide 16 are incident on the loading material 282 and are reflected back toward the central portion of the waveguide aperture. The energy distribution afforded by the horn loading material 282 is again substantially uniform across the central portion of the waveguide aperture and drops off sharply toward the perimeter.

It will be appreciated that the horn 16 of the preferred embodiment which supports multiple odd-numbered harmonic modes of wave propagation can provide a substantially uniform electromagnetic field across the central portion of the horn aperture at low power settings without the benefit of either the conductive grid 55, the differential dielectric lens 250, or the horn loading material 282. Similarly, at low power settings, a waveguide supporting only a single mode of wave propagation can provide a substantially uniform field when the wave pattern is "tweaked" by a conductive grid 55, a dielectric lens 250, or horn loading material 282. However, optimum power settings, when the multiple odd-numbered harmonic modes of propagation are augmented with the wave pattern redistribution means.

It will be understood that terms such as "upper" and "lower" are employed herein for convenience of description and are not meant to limit the invention to any particular orientation. In particular, certain advantages may be obtained by inverting the waveguide and cap assembly so that the magnetron is at the upper end of the waveguide and the flared end of the horn is at the bottom. The cap assembly would thus translate against the lower end of the horn. The advantage to be derived is that as the plasma begins to thaw, the liquid plasma, which is denser than solid plasma, will migrate toward the bottom of the bag and away from the magnetron. The liquid plasma will thus not "shadow" frozen plasma distal to the microwave source. Instead, the frozen plasma will be interposed between the microwave source and the liquid plasma, the frozen plasma thereby receiving the full illumination of the microwave energy and somewhat shielding the liquid plasma. Such an orientation thus further serves to inhibit "thermal runaway."

The detail description hereinabove set forth is not intended to limit the invention to any particular embodiment. For example, while the preferred embodiment is disclosed with respect to a microwave illuminator employing a magnetron for generating microwaves, it will be understood that other suitable mechanisem, for example, a klystron, may be substituted. Similarly, linear actuators with limit stops may be substituted for the pneumatic cylinders of the disclosed embodiment to raise and lower the cap assembly. Also, while infrared fiber optic sensors are disclosed in the preferred embodiment, other appropriate sensing devices may be employed.

While the preferred embodiment is disclosed with respect to a microwave illuminator especially adapted for thawing frozen plasma, it will be appreciated that the present invention is easily adaptable for thawing other cryopreserved fluids and tissue, such as whole blood, erythrocytes, or frozen heart valves, without departing from the scope and spirit of the appended claims.

Finally, it will be understood that other modifications may occur to those skilled in the art without departing from the scope and spirit of the appended claims.

What is claimed is:

1. An apparatus for thawing a frozen material, comprising:
   a microwave generator selectively operable to generate microwaves;
   a hollow waveguide for confining and guiding said microwaves to propagate in a plurality of odd-numbered modes of propagations, aid waveguide defining an axis of propagation and being configured such that at a predetermined point along said axis of propagation the cumulative effect of said plurality of odd-numbered modes of propagation creates an approximately uniform electromagnetic field across a predetermined transverse cross section of said waveguide, said waveguide further defining a reservoir therein such that said reservoir can be filled with a liquid dielectric medium;
   a first flexible membrane for supporting a frozen material to be thawed thereupon, said first flexible membrane being disposed transversely to said axis of propagation at said predetermined point along said axis of propagation; and
   a cap assembly having an opening at one end thereof and defining a cavity therein, said cap assembly including a second flexible membrane sealing said opening at said one end of said cap assembly such that said cavity in said cap assembly is capable of containing a liquid therein, and said cap assembly being mounted adjacent said hollow waveguide and translatable to bring said second flexible membrane at said one end of said cap assembly into engagement with a frozen material to be thawed supported on said first flexible membrane;
   whereby when said material to be thawed is positioned between said first and second flexible membranes and said cap assembly is translated, said flexible membranes intimately conform to said material to be thawed such that said first and second membranes completely encapsulate said material to be thawed;
   whereby when said material to be thawed is so encapsulated between said first and second flexible membranes and said reservoir in said hollow waveguide and said cavity in said cap assembly are filled with a liquid dielectric medium, said material to be thawed is surrounded by said liquid dielectric medium; and
   whereby said electromagnetic field at said predetermined point along said axis of propagation heats said material to be thawed.

2. The apparatus of claim 1, further comprising an oil contained within said reservoir in said hollow waveguide and within said cavity in said cap assembly, said oil having a dielectric constant substantially equal to the dielectric constant of the material being thawed.

3. The apparatus of claim 1, further comprising means operatively associated with said waveguide for redistributing said generated microwaves to provide a more uniform electromagnetic field across said predetermined transverse cross section of said waveguide in the direction of electromagnetic intensity of said microwaves.

4. The thawing apparatus of claim 3, wherein said means operatively associated with said waveguide for redistributing said generated microwaves to provide a substantially uniform electromagnetic field across said aperture of said waveguide in the direction of electromagnetic intensity of said microwaves comprises a conductive grid disposed substantially transverse to said axis of propagation for reflecting electromagnetic waves at predetermined locations thereon.

5. The thawing apparatus of claim 4, wherein said conductive grid is disposed substantially transverse to said axis of propagation and defines a plurality of slots therein.

6. The thawing apparatus of claim 3, wherein said means operatively associated with said waveguide for redistributing said generated microwaves to provide a substantially uniform electromagnetic field across said predetermined transverse cross section of said waveguide in the direction of electromagnetic intensity of said microwaves comprises means for refracting said electromagnetic waves to provide a substantially uniform electromagnetic field.

7. The thawing apparatus of claim 6, wherein said refracting means comprises a differential dielectric focusing medium.

8. The thawing apparatus of claim 7, wherein said differential dielectric focusing medium comprises a dielectric lens disposed substantially transverse to the direction of propagation of said generated microwaves and comprised of a material having a dielectric constant different than that of the medium in which it is disposed.

9. The thawing apparatus of claim 7, wherein said differential dielectric focusing medium comprises a material disposed within said hollow waveguide at locations proximate the outer edges thereof for refracting said electromagnetic waves to provide a substantially uniform electromagnetic field.

10. The thawing apparatus of claim 1, further comprising a microwave absorber disposed above said cap assembly, whereby microwaves which are not absorbed by said material being thawed are dissipated.

11. The thawing apparatus of claim 1, further comprising fluid regulating means operatively associated with said reservoir in said hollow waveguide and said cavity in said cap assembly such that when said reservoir and said cavity are filled with a liquid dielectric medium, said fluid regulating means is operative to maintain a desired pressure against said flexible membranes and to compensate for volume changes in the liquid dielectric medium resulting from displacement by said material being thawed.

12. The thawing apparatus of claim 1, wherein said hollow waveguide comprises an RF horn.

13. The thawing apparatus of claim 1, wherein said first and second flexible membranes are comprised of a material having a dielectric constant substantially equal to that of the frozen material being thawed, whereby dielectric discontinuities at the interfaces between said membranes and said material being thawed are eliminated.

14. The apparatus of claim 1, further comprising means for preventing a major portion of said microwaves which propagate through said frozen material being thawed from being reflected back into said hollow waveguide.

15. The apparatus of claim 14, wherein said means for preventing a major portion of said microwaves which propagate through said frozen material being thawed from being reflected back into said hollow waveguide comprises a tank of water disposed at a point along said axis of propagation opposite said predetermined transverse cross section of said waveguide from said microwave generator.

16. The apparatus of claim 15, wherein said tank of water comprises lower walls angled at less than 45° with respect to said axis of propagation, whereby any microwaves reflected off one of said lower walls will be reflected to another of said angled walls and into said tank.

17. The apparatus of claim 1, further comprising an RF-shielded cabinet enclosing said apparatus, whereby microwaves generated by said microwave generator are contained within said cabinet.

18. The apparatus of claim 1, further comprising means for detecting the temperature of said frozen material as it is being thawed, and for deactivating said microwave generator when said frozen material has reached a predetermined temperature.

19. An apparatus for thawing a frozen material, comprising:
a microwave generator selectively operable to generate microwaves;
a hollow wave guide for confining and guiding the propagation of said microwaves, said wave guide having an aperture at one end and defining a reservoir therein, whereby said reservoir of said wave guide can be filled with a liquid dielectric medium;
a first flexible membrane covering said aperture at said one end of said wave guide;
a cap assembly open at one end and defining a cavity therein, said cap assembly being mounted adjacent said hollow waveguide and translatable to bring said one end of said cap assembly into engagement with said one end of said waveguide;
a second flexible membrane sealing said opening at said one end of said cap assembly such that said cavity in said assembly is capable of containing a liquid therein, whereby said cavity of said cap assembly can be filled with a liquid dielectric medium; and
means operatively associated with said waveguide for redistributing said generated microwaves to provide a substantially uniform electromagnetic field across said aperture of said waveguide in the direction of electromagnetic intensity of said microwaves;
whereby when a material being thawed is positioned between said first and second flexible membranes and said cap assembly is translated against said one end of said hollow waveguide, said flexible membranes intimately conform to said material being thawed such that said first and second membranes completely encapsulate said material being thawed;
whereby when said material being thawed is so encapsulated between said first and second flexible membranes and said reservoir in said hollow waveguide and said cavity in said cap assembly are filled with a liquid dielectric medium, said material being thawed is surrounded by said liquid dielectric medium; and
whereby said electromagnetic field across said aperture of said hollow waveguide heats said material being thawed.

20. The thawing apparatus of claim 19, further comprising a microwave absorber disposed above said cap assembly, whereby microwaves which are not absorbed by said material being thawed are dissipated.

21. The apparatus of claim 20, wherein said microwave absorber comprises a tank of water.

22. The thawing apparatus of claim 19, further comprising fluid regulating means operatively associated with said reservoir in said hollow waveguide and said cavity in said cap assembly such that when said reservoir and said cavity are filled with a liquid dielectric medium, said fluid regulating means is operative to maintain a desired pressure against said flexible membranes and to compensate for volume changes in the liquid dielectric medium resulting from displacement by said material being thawed.

23. The thawing apparatus of claim 19, wherein said means operatively associated with said waveguide for redistributing said generated microwaves to provide a substantially uniform electromagnetic field across said aperture of said waveguide in the direction of electromagnetic intensity of said microwaves comprises a conductive grid disposed substantially transverse to said axis of propagation for reflecting electromagnetic waves at predetermined locations thereon.

24. The thawing apparatus of claim 23, wherein said conductive grid is disposed substantially transverse to said axis of propagation and defines a plurality of slots therein.

25. The thawing apparatus of claim 19, wherein said means operatively associated with said waveguide for redistributing said generated microwaves to provide a substantially uniform electromagnetic field across said aperture of said waveguide in the direction of electromagnetic intensity of said microwaves comprises means for refracting said electromagnetic waves to provide a substantially uniform electromagnetic field.

26. The thawing apparatus of claim 25, wherein said refracting means comprises a differential dielectric focusing medium.

27. The thawing apparatus of claim 26, wherein said differential dielectric focusing medium comprises a dielectric lens disposed substantially transverse to the direction of propagation of said generated microwaves and comprised of a material having a dielectric constant different than that of the medium in which it is disposed.

28. The thawing apparatus of claim 26, wherein said differential dielectric focusing medium comprises a material disposed within said hollow waveguide at locations proximate the outer edges thereof for refracting said electromagnetic waves to provide a substantially uniform electromagnetic field.

29. The thawing apparatus of claim 19, wherein said hollow waveguide comprises an RF horn.

30. The thawing apparatus of claim 19, wherein said first and second flexible membranes are comprised of a material having a dielectric constant substantially equal to that of the frozen material being thawed, whereby dielectric discontinuities at the interfaces between said membranes and said material being thawed are eliminated.

31. The apparatus of claim 19, further comprising an RF-shielded cabinet enclosing said apparatus, whereby microwaves generated by said microwave generator are contained within said cabinet.

32. The apparatus of claim 19, further comprising means for detecting the temperature of said frozen material as it is being thawed, and for deactivating said microwave generator when said frozen material has reached a predetermined temperature.

33. An apparatus for thawing a container of frozen plasma, comprising:
a microwave generator selectively operable to generate microwaves;
a hollow waveguide for confining and guiding the propagation of said microwaves, said hollow waveguide having an aperture at one end and defining a reservoir therein;
a first flexible membrane covering said aperture at said one end of said hollow waveguide, said first flexible membrane being comprised of a material having a dielectric constant substantially equal to the dielectric constant of frozen plasma;
a cap assembly mounted adjacent said hollow waveguide and translatable against said one end thereof, said cap assembly defining a cavity therein which is open at one end;
a second flexible membrane sealing said opening at said one end of said cavity in said cap assembly such that said cavity in said cap assembly is capable of containing a liquid therein, said second flexible membrane being comprised of a material having a dielectric constant substantially equal to the dielectric constant of frozen plasma;
a liquid dielectric medium filling said reservoir in said hollow waveguide and said cavity in said cap assembly and having a dielectric constant substantially equal to the dielectric constant of frozen plasma; and
a differential dielectric focusing medium disposed within said hollow waveguide for refracting said generated microwaves propagating within said hollow waveguide to provide a substantially uniform electromagnetic field across said aperture of said waveguide in the direction of electromagnetic intensity of said microwaves;
whereby when a container of frozen plasma is positioned between said first and second flexible membranes and said cap assembly is translated against said one end of said hollow waveguide, said flexible membranes intimately conform to said container of frozen plasma such that said first and second membranes encapsulate said container of frozen plasma;
whereby when said container of frozen plasma is so encapsulated between said first and second flexible membranes, said container of frozen plasma is surrounded by said liquid dielectric medium having a dielectric constant substantially equal to the dielectric constant of the frozen material being thawed, and interfaces between materials of differing dielectric constants which can distort said electromagnetic field across said aperture of said waveguide and cause nonuniform heating of said container of frozen plasma are minimized; and
whereby said container of froze plasma is heated by said electromagnetic field across said aperture of said waveguide, said liquid dielectric medium surrounding said container of frozen plasma serving as a thermal damper, absorbing and dissipating any uneven heating within said frozen plasma such said frozen plasma will heat uniformly.

34. The apparatus of claim 33, wherein said first and second flexible membranes are comprised of polyvinyl chloride.

35. The apparatus of claim 33, wherein said hollow waveguide comprises a horn having four substantially planar sides tapering outwardly toward said one end.

36. The apparatus of claim 33, wherein said microwave generator comprises a magnetron having an antenna disposed within the end of said hollow waveguide opposite said one end.

37. The apparatus of claim 33, further comprising means for preventing a major portion of said microwaves which propagate through said frozen plasma from being reflected back into said hollow waveguide.

38. The apparatus of claim 37, wherein said means for preventing a major portion of said microwaves which propagate through said frozen plasma being thawed from being reflected back into said hollow waveguide comprises a tank of water disposed at a point on the side of said second flexible membrane which is opposite said microwave generator.

39. The apparatus of claim 38, wherein said tank of water comprises lower walls angled at less than 45° with respect to said axis of propagation, whereby any microwaves reflected off one of said lower walls will be reflected to another of said angled walls and into said tank.

40. The apparatus of claim 33, further comprising an RF-shielded cabinet enclosing said apparatus, whereby microwaves generated by said microwave generator are contained within said cabinet.

41. The apparatus of claim 33, further comprising means for detecting the temperature of said frozen plasma as it is being thawed, and for deactivating said microwave generator when said frozen plasma has reached a predetermined temperature.

42. The apparatus of claim 33, further comprising means for detecting that a substance positioned between said first and second flexible membranes is not a container of frozen plasma, and for deactivating said microwave generator in response to said detection.

43. The apparatus of claim 33, wherein said first and second flexible membranes are dimensioned to accommodate two containers of frozen plasma.

44. A microwave illuminator for thawing a container of frozen plasma, comprising:
an electromagnetic energy source selectively operable to generate electromagnetic waves;
a hollow waveguide having first and second ends, said electromagnetic energy source being disposed at said first end of said waveguide, said waveguide having an aperture of a predetermined area at said second end, said hollow waveguide defining a reservoir therein, and said waveguide being operative to confine and to guide said microwaves to propagate in a plurality of odd-numbered modes of propagation such that the cumulative effect of said plurality of odd-numbered modes of propagation creates an approximately uniform electromagnetic field across said aperture at said second end of said waveguide;
a first flexible membrane covering said aperture at said second end of said waveguide, said first flexible membrane being comprised of a material having a dielectric constant substantially equal to the dielectric constant of frozen plasma;
a cap assembly having an opening at one end thereof, said cap assembly being mounted adjacent said second end of said waveguide and being translatable to bring said one end of said cap assembly into engagement with said second end of said waveguide, said cap assembly defining a cavity therein;

a second flexible membrane sealing said opening at said one end of said cap assembly such that said cavity in said cap assembly is capable of containing a liquid therein, said second flexible membrane being comprised of a material having a dielectric constant substantially equal to the dielectric constant of frozen plasma; and a liquid dielectric medium filling said reservoir in said hollow waveguide and said cavity in said cap assembly and having a dielectric constant substantially equal to the dielectric constant of frozen plasma;

whereby when a container of frozen plasma is positioned in said aperture at said second end of said waveguide and said cap assembly is translated against said second end of said hollow waveguide, said first and second flexible membranes intimately conform to said container of frozen plasma such that said first and second membranes encapsulate said container of frozen plasma;

whereby when said container of frozen plasma is so encapsulated between said first and second flexible membranes, dielectric discontinuities between said electromagnetic energy source and which can distort said electromagnetic field across said aperture of said waveguide and cause nonuniform heating of said container of frozen plasma are minimized; and whereby said container of frozen plasma is heated by said electromagnetic field across said aperture of said waveguide, said liquid dielectric medium surrounding said container of frozen plasma serving as a thermal damper, absorbing and dissipating any uneven heating within said frozen plasma such said frozen plasma will heat uniformly.

45. The microwave illuminator of claim 44, further comprising means for preventing a major portion of said electromagnetic waves which propagate through said frozen plasma from being reflected back into said hollow waveguide.

46. The microwave illuminator of claim 45, wherein said means for preventing a major portion of said electromagnetic waves which propagate through said frozen plasma from being reflected back into said hollow waveguide comprises a tank of water disposed at a point beyond said aperture from said electromagnetic energy source.

47. The microwave illuminator of claim 44, further comprising an RF-shielded cabinet enclosing said apparatus, whereby electromagnetic waves generated by said electromagnetic energy source are contained within said cabinet.

48. The microwave illuminator of claim 44, further comprising means for detecting the temperature of said frozen plasma as it is being thawed, and for deactivating said electromagnetic energy source when said frozen plasma has reached a predetermined temperature.

49. The microwave illuminator of claim 44, further comprising means for detecting that a substance positioned in said aperture is not a container of frozen plasma, and for deactivating said electromagnetic energy source in response to said detection.

50. The apparatus of claim 44, wherein said first and second flexible membranes are dimensioned to accommodate two containers of frozen plasma.

51. A microwave illuminator for thawing a container of frozen plasma, comprising:

an electromagnetic energy source selectively operable to generate electromagnetic waves;

a hollow waveguide having first and second ends, said electromagnetic energy source being disposed at said first end of said waveguide, said waveguide having an aperture of a predetermined area at said second end, said hollow waveguide defining a reservoir therein, and said waveguide being operative to project and to convey said electromagnetic waves and to disperse said electromagnetic waves across said predetermined area of said aperture at said second end of said waveguide;

a conductive grid disposed within said hollow waveguide for redistributing said electromagnetic waves to provide an electromagnetic field of substantially uniform intensity across said aperture at said second end of said waveguide in the direction of electromagnetic intensity of said electromagnetic waves;

a first flexible membrane covering said aperture at said second end of said waveguide, said first flexible membrane being comprised of a material having a dielectric constant substantially equal to the dielectric constant of frozen plasma;

a cap assembly having an opening at one end thereof, said cap assembly being mounted adjacent said second end of said waveguide and being translatable to bring said one end of said cap assembly into engagement with said second end of said waveguide, said cap assembly defining a cavity therein;

a second flexible membrane sealing said opening at said one end of said cap assembly such that said cavity in said cap assembly is capable of containing a liquid therein, said second flexible membrane being comprised of a material having a dielectric constant substantially equal to the dielectric constant of frozen plasma; and a liquid dielectric medium filling said reservoir in said hollow waveguide and said cavity in said cap assembly and having a dielectric constant substantially equal to the dielectric constant of frozen plasma;

whereby when a container of frozen plasma is positioned in said aperture at said second end of said waveguide and said cap assembly is translated against said second end of said hollow waveguide, said first and second flexible membranes intimately conform to said container of frozen plasma such that said first and second membranes encapsulate said container of frozen plasma;

whereby when said container of frozen plasma is so encapsulated between said first and second flexible membranes, dielectric discontinuities between said electromagnetic energy source and which can distort said electromagnetic field across said aperture of said waveguide and cause nonuniform heating of said container of frozen plasma are minimized; and whereby said container of frozen plasma is heated by said electromagnetic field across said aperture of said waveguide, said liquid dielectric medium surrounding said container of frozen plasma serving as a thermal damper, absorbing and dissipating any uneven heating within said frozen plasma such said frozen plasma will heat uniformly.

52. The microwave illuminator of claim 51, further comprising means for preventing a major portion of said electromagnetic waves which propagate through said frozen plasma from being reflected back into said hollow waveguide.

53. The microwave illuminator of claim 52, wherein said means for preventing a major portion of said electromagnetic waves which propagate through said frozen plasma from being reflected back into said hollow waveguide comprises a tank of water disposed at a point beyond said aperture from said electromagnetic energy source.

54. The microwave illuminator of claim 51, further comprising an RF-shielded cabinet enclosing said apparatus, whereby electromagnetic waves generated by said electromagnetic energy source are contained within said cabinet.

55. The microwave illuminator of claim 51, further comprising means for detecting the temperature of said frozen plasma as it is being thawed, and for deactivating said electromagnetic energy source when said frozen plasma has reached a predetermined temperature.

56. The microwave illuminator of claim 51, further comprising means for detecting that a substance positioned in said aperture is not a container of frozen plasma, and for deactivating said electromagnetic energy source in response to said detection.

57. The apparatus of claim 51, wherein said first and second flexible membranes are dimensioned to accommodate two containers of frozen plasma.

58. A microwave illuminator for thawing a container of frozen plasma, comprising:
    an electromagnetic energy source selectively operable to generate electromagnetic waves;
    a hollow waveguide having first and second ends, said electromagnetic energy source being disposed at said first end of said waveguide, said waveguide having an aperture of a predetermined area at said second end, said hollow waveguide defining a reservoir therein, and said waveguide being operative to confine and to guide said microwaves to propagate in a plurality of odd-numbered modes of propagation and to disperse said electromagnetic waves across said predetermined area of said aperture at said second end of said waveguide;
    a conductive grid disposed within said hollow waveguide for redistributing said electromagnetic waves to provide an electromagnetic field of substantially uniform intensity across said aperture at said second end of said waveguide in the direction of electromagnetic intensity of said electromagnetic waves;
    a first flexible membrane covering said aperture at said second end of said waveguide, said first flexible membrane being comprised of a material having a dielectric constant substantially equal to the dielectric constant of frozen plasma;
    a cap assembly having an opening at one end thereof, said cap assembly being mounted adjacent said second end of said waveguide and being translatable to bring said one end of said cap assembly into engagement with said second end of said waveguide, said cap assembly defining a cavity therein;
    a second flexible membrane sealing said opening at said one of said cap assembly such that said cavity in said cap assembly is capable of containing a liquid therein, said second flexible membrane being comprised of a material having a dielectric constant substantially equal to the dielectric constant of frozen plasma; and
    a liquid dielectric medium filling said reservoir in said hollow waveguide and said cavity in said cap assembly and having a dielectric constant substantially equal to the dielectric constant of frozen plasma;
    whereby when a container of frozen plasma is positioned in said aperture at said second end of said waveguide and said cap assembly is translated against said second end of said hollow waveguide, said first and second flexible membranes intimately conform to said container of frozen plasma such that said first and second membranes encapsulate said container of frozen plasma;
    whereby when said container of frozen plasma is so encapsulated between said first and second flexible membranes, dielectric discontinuities between said electromagnetic energy source and which can distort said electromagnetic field across said aperture of said waveguide and cause nonuniform heating of said container of frozen plasma are minimized; and
    whereby said container of frozen plasma is heated by said electromagnetic field across said aperture of said waveguide, said liquid dielectric medium surrounding said container of frozen plasma serving as a thermal damper, absorbing and dissipating any uneven heating within said frozen plasma such said frozen plasma will heat uniformly.

59. The microwave illuminator of claim 58, further comprising means for preventing a major portion of said electromagnetic waves which propagate through said frozen plasma being reflected back into said hollow waveguide.

60. The microwave illuminator of claim 59, wherein said means for preventing a major portion of said electromagnetic waves which propagate through said frozen plasma from being reflected back into said hollow waveguide comprises a tank of water disposed at a point beyond said aperture from said electromagnetic energy source.

61. The microwave illuminator of claim 58, further comprising an RF-shielded cabinet enclosing said apparatus, whereby electromagnetic waves generated by said electromagnetic energy source are contained within said cabinet.

62. The microwave illuminator of claim 58, further comprising means for detecting the temperature of said frozen plasma as it is being thawed, and for deactivating said electromagnetic energy source when said frozen plasma has reached a predetermined temperature.

63. The microwave illuminator of claim 58, further comprising means for detecting that a substance positioned in said aperture is not a container of frozen plasma, and for deactivating said electromagnetic energy source in response to said detection.

64. The apparatus of claim 58, wherein said first and second flexible membranes are dimensioned to accommodate two containers of frozen plasma.

* * * * *